United States Patent
Hermon-Taylor

(10) Patent No.: US 12,203,934 B2
(45) Date of Patent: *Jan. 21, 2025

(54) **METHOD OF DETECTING *MYCOBACTERIUM AVIUM* SUBSPECIES PARATUBERCULOSIS INFECTION**

(71) Applicant: HAV VACCINES LIMITED, Milton Keynes (GB)

(72) Inventor: John Hermon-Taylor, London (GB)

(73) Assignee: HAV VACCINES LIMITED, Milton Keynes (GB)

( * ) Notice: Subject to any disclaimer, the term of this patent is extended or adjusted under 35 U.S.C. 154(b) by 0 days.

This patent is subject to a terminal disclaimer.

(21) Appl. No.: 18/332,263

(22) Filed: Jun. 9, 2023

(65) Prior Publication Data

US 2023/0400462 A1 Dec. 14, 2023

Related U.S. Application Data

(63) Continuation of application No. 17/348,428, filed on Jun. 15, 2021, now Pat. No. 11,714,085, which is a continuation of application No. 16/476,656, filed as application No. PCT/GB2018/050075 on Jan. 11, 2018, now abandoned.

(30) Foreign Application Priority Data

Jan. 11, 2017 (GB) ..................................... 1700487

(51) Int. Cl.
*G01N 33/569* (2006.01)
*C07K 14/35* (2006.01)
*C07K 16/12* (2006.01)

(52) U.S. Cl.
CPC ......... *G01N 33/5695* (2013.01); *C07K 14/35* (2013.01); *C07K 16/1289* (2013.01); *C07K 2317/34* (2013.01); *G01N 2333/35* (2013.01)

(58) Field of Classification Search
None
See application file for complete search history.

(56) References Cited

U.S. PATENT DOCUMENTS

| | | | |
|---|---|---|---|
| 5,225,324 | A | 7/1993 | McFadden et al. |
| 6,156,322 | A | 12/2000 | Hermon-Taylor et al. |
| 7,541,181 | B2 | 6/2009 | Hermon-Taylor et al. |
| 7,892,566 | B2 | 2/2011 | Hermon-Taylor et al. |
| 8,147,850 | B2 | 4/2012 | Hermon-Taylor et al. |
| 11,714,085 | B2 | 8/2023 | Hermon-Taylor |
| 2005/0112139 | A1 | 5/2005 | Karp |
| 2011/0129502 | A1 | 6/2011 | Hermon-Taylor et al. |
| 2020/0041509 | A1 | 2/2020 | Hermon-Taylor |

FOREIGN PATENT DOCUMENTS

| | | |
|---|---|---|
| EP | 0288306 | 10/1988 |
| WO | WO 88/08456 | 11/1988 |
| WO | WO 97/23624 | 7/1997 |
| WO | WO 99/49054 | 9/1999 |
| WO | WO 2007/017635 | 2/2007 |
| WO | WO 2010/142423 | 12/2010 |
| WO | WO 2011/013034 | 2/2011 |
| WO | WO 2012/159121 | 11/2012 |
| WO | WO 2014/016737 | 1/2014 |

OTHER PUBLICATIONS

International Search Report and Written Opinion prepared by the European Patent Office on Apr. 26, 2018, for International Application No. PCT/GB2018/050075.
Almagro et al. "Humanization of antibodies," Frontiers in Bioscience, Jan. 2008, vol. 13, pp. 1619-1633.
Botsaris et al. "Detection of viable *Mycobacterium avium* subspecies paratuberculosis in powdered infant formula by phage-PCR and confirmed culture," International Journal of Food Microbiology, 2016, vol. 216, pp. 91-94.
Bull et al. "Immunity, safety and protection of an Adenovirus 5 prime—Modified Vaccinia virus Ankara boost subunit vaccine against *Mycobacterium avium* subspecies paratuberculosis infection in calves," Veterinary Research, 2014, vol. 45, 112, 17 pages.
Bull et al. "Detection and Verification of *Mycobacterium avium* subsp. Paratuberculosis in Fresh Ileocolonic Mucosal Biopsy Specimens from Individuals with and without Crohn's Disease," Journal of Clinical Microbiology, Jul. 2003, vol. 41, No. 7, pp. 2915-2923.
Edwards et al. "The Remarkable Flexibility of the Human Antibody Repertoire; Isolation of Over One Thousand Different Antibodies to a Single Protein, BLyS," Journal of Molecular Biology, 2003, vol. 334, pp. 103-118.
Fridy et al. "A robust pipeline for rapid production of versatile nanobody repertoires," Nature Methods, Dec. 2014, vol. 11, No. 12, pp. 1253-1260.
Green et al. "Sequence and characteristics of IS900, an insertion element identified in a human Crohn's disease isolate of *Mycobacterium paratuberculosis*," Nucleic Acids Research, 1989, vol. 17, No. 22, pp. 9063-9073.
Hermon-Taylor "*Mycobacterium avium* subspecies paratuberculosis, Crohn's disease and the Doomsday Scenario," Gut Pathogens, Feb. 2009, 1:15, 7 pages.
Li et al. "The complete genome sequence of *Mycobacterium avium* subspecies paratuberculosis," PNAS, Aug. 2005, vol. 102, No. 35, pp. 12344-12349.

(Continued)

*Primary Examiner* — Oluwatosin A Ogunbiyi

(74) *Attorney, Agent, or Firm* — Sheridan Ross P.C.

(57) ABSTRACT

A method of diagnosing or monitoring *Mycobacterium avium* subspecies paratuberculosis (MAP) infection, which method comprises detecting the presence of the polypeptide (MAP P900) encoded by the positive strand of IS900, or a fragment thereof, in a sample from a subject, wherein MAP P900, or a fragment thereof, is detected using an antibody, or an antigen-binding fragment thereof, that binds to MAP P900.

17 Claims, 9 Drawing Sheets

Specification includes a Sequence Listing.

(56) References Cited

OTHER PUBLICATIONS

Li et al. "Early detection of *Mycobacterium avium* subsp. Paratuberculosis infection in cattle with multiplex-bead based immunoassays," PLOS One, Dec. 2017, vol. 12, No. 12, e0189783, 16 pages.

Nacy et al. "*Mycobacterium avium* Paratuberculosis: Infrequent Human pathogen or Public Health Threat?" American Academy of Microbiology, 2008, 41 pages.

Naser et al. "In situ identification of mycobacteria in Crohn's disease patient tissue using confocal scanning laser microscopy," Molecular and Cellular Probes, 2002, vol. 16, pp. 41-48.

Ricchi et al. "Exploring MALDI-TOF MS approach for a rapid identification of *Mycobacterium avium* ssp. Paratuberculosis field isolates," Journal of Applied Microbiology, 2016, vol. 122, pp. 568-577.

Scanu et al. "*Mycobacterium avium* Subspecies paratuberculosis Infection in Cases of Irritable Bowel Syndrome and Comparison with Crohn's Disease and Johne's Disease: Common Neural and Immune Pathogenicities," Journal of Clinical Microbiology, Dec. 2007, vol. 45, No. 12, pp. 3883-3890.

Sheridan "Ablynx's nanobody fragments go places antibodies cannot," Nature Biotechnology, Dec. 2017, vol. 34, No. 12, pp. 1115-1117.

Tizard et al. "p43, the protein product of the atypical insertion sequence IS900, is expressed in *Mycobacterium paratuberculosis*," Journal of General Microbiology, Aug. 1992, vol. 138, No. 8, pp. 1729-1736.

Van Der Burg et al. "Vaccines for established cancer: overcoming the challenges posed by immune evasion," Nature Reviews Cancer, Apr. 2016, vol. 16, pp. 219-233.

Official Action for U.S. Appl. No. 16/476,656, dated Sep. 14, 2020 9 pages Restriction Requirement.

Official Action for U.S. Appl. No. 16/476,656, dated Jan. 19, 2021 14 pages.

Official Action for U.S. Appl. No. 17/348,428, dated Sep. 22, 2022 12 pages.

Notice of Allowance for U.S. Appl. No. 17/348,428, dated Mar. 15, 2023 5 pages.

Di Sabatino et al. "Detection of *Mycobacterium avium* subsp. Paratuberculosis (MAP)-specific IS900 DNA and Antibodies Against MAP Peptides and Lysate in the Blood of Crohn's Disease Patients," Inflammatory Bowel Diseases, May 2011, vol. 17, No. 5, pp. 1254-1255.

SEQUENCE LISTING

```
Sequence total quantity: 98
SEQ ID NO: 1                    moltype = AA  length = 406
FEATURE                         Location/Qualifiers
source                          1..406
                                mol_type = protein
                                note = paratuberculosis
                                organism = Mycobacterium avium
SEQUENCE: 1
MTVTEVVVAQ PVWAGVDAGK ADHYCMVIND DAQRLLSQRV ANDEAALLEL IAAVTTLADG    60
GEVTWAIDLN AGGAALLIAL LIAAGQRLLY IPGRTVHHAA GSYRGEGKTD AKDAAIIADQ   120
ARMRHDLQPL RAGDDIAVEL RILTSRRSDL VADRTRAINR MRAQLLEYFP ALERAFDYNK   180
SRAALILLTG YQTPDALRSA GGARVAAFLR KRKARNADTV AATALQAANA QHSIVPGQQL   240
AATVVARLAK EVMALDTEIG DTDAMIEERF RRHRHAEIIL SMPGFGVILG AEFLAATGGD   300
MAAFASADRL AGVAGLAPVP RDSGRISGNL KRPRRYDRRL LRACYLSALV SIRTDPSSRT   360
YYDRKRTEGK RHTQAVLALA RRRLNVLWAM LRDHAVYHPA TTTAAA                  406

SEQ ID NO: 2                    moltype = AA  length = 14
FEATURE                         Location/Qualifiers
source                          1..14
                                mol_type = protein
                                note = paratuberculosis
                                organism = Mycobacterium avium
SEQUENCE: 2
MVINDDAQRL LSQR                                                      14

SEQ ID NO: 3                    moltype = AA  length = 14
FEATURE                         Location/Qualifiers
MOD_RES                         12
                                note = PHOSPHORYLATION
source                          1..14
                                mol_type = protein
                                note = paratuberculosis
                                organism = Mycobacterium avium
SEQUENCE: 3
MVINDDAQRL LSQR                                                      14

SEQ ID NO: 4                    moltype = AA  length = 15
FEATURE                         Location/Qualifiers
source                          1..15
                                mol_type = protein
                                note = paratuberculosis
                                organism = Mycobacterium avium
SEQUENCE: 4
YLSALVSIRT DPSSR                                                     15

SEQ ID NO: 5                    moltype = AA  length = 10
FEATURE                         Location/Qualifiers
source                          1..10
                                mol_type = protein
                                note = paratuberculosis
                                organism = Mycobacterium avium
SEQUENCE: 5
VSIRTDPSSR                                                           10

SEQ ID NO: 6                    moltype = AA  length = 15
FEATURE                         Location/Qualifiers
MOD_RES                         14
                                note = PHOSPHORYLATION
source                          1..15
                                mol_type = protein
                                note = paratuberculosis
                                organism = Mycobacterium avium
SEQUENCE: 6
YLSALVSIRT DPSSR                                                     15

SEQ ID NO: 7                    moltype = AA  length = 15
FEATURE                         Location/Qualifiers
MOD_RES                         13
                                note = PHOSPHORYLATION
source                          1..15
                                mol_type = protein
                                note = paratuberculosis
                                organism = Mycobacterium avium
SEQUENCE: 7
YLSALVSIRT DPSSR                                                     15

SEQ ID NO: 8                    moltype = AA  length = 10
FEATURE                         Location/Qualifiers
```

```
MOD_RES              8..9
                     note = PHOSPHORYLATION
source               1..10
                     mol_type = protein
                     note = paratuberculosis
                     organism = Mycobacterium avium
SEQUENCE: 8
VSIRTDPSSR                                                              10

SEQ ID NO: 9         moltype = AA  length = 10
FEATURE              Location/Qualifiers
MOD_RES              8
                     note = PHOSPHORYLATION
source               1..10
                     mol_type = protein
                     note = paratuberculosis
                     organism = Mycobacterium avium
SEQUENCE: 9
VSIRTDPSSR                                                              10

SEQ ID NO: 10        moltype = AA  length = 17
FEATURE              Location/Qualifiers
source               1..17
                     mol_type = protein
                     note = paratuberculosis
                     organism = Mycobacterium avium
SEQUENCE: 10
AAVTTLADGG EVTWAID                                                      17

SEQ ID NO: 11        moltype = AA  length = 15
FEATURE              Location/Qualifiers
source               1..15
                     mol_type = protein
                     note = paratuberculosis
                     organism = Mycobacterium avium
SEQUENCE: 11
NLKRPRRYDR RLLRA                                                        15

SEQ ID NO: 12        moltype = AA  length = 15
FEATURE              Location/Qualifiers
source               1..15
                     mol_type = protein
                     note = paratuberculosis
                     organism = Mycobacterium avium
SEQUENCE: 12
VTTLADGGEV TWAID                                                        15

SEQ ID NO: 13        moltype = AA  length = 15
FEATURE              Location/Qualifiers
MOD_RES              13..14
                     note = PHOSPHORYLATION
source               1..15
                     mol_type = protein
                     note = paratuberculosis
                     organism = Mycobacterium avium
SEQUENCE: 13
YLSALVSIRT DPSSR                                                        15

SEQ ID NO: 14        moltype = AA  length = 21
FEATURE              Location/Qualifiers
source               1..21
                     mol_type = protein
                     note = paratuberculosis
                     organism = Mycobacterium avium
SEQUENCE: 14
YCMVINDDAQ RLLSQRVAND E                                                 21

SEQ ID NO: 15        moltype = AA  length = 20
FEATURE              Location/Qualifiers
source               1..20
                     mol_type = protein
                     note = paratuberculosis
                     organism = Mycobacterium avium
SEQUENCE: 15
AAVTTLADGG EVTWAIDLNA                                                   20

SEQ ID NO: 16        moltype = AA  length = 32
FEATURE              Location/Qualifiers
source               1..32
```

-continued

```
                              mol_type = protein
                              note = paratuberculosis
                              organism = Mycobacterium avium
SEQUENCE: 16
NLKRPRRYDR RLLRACYLSA LVSIRTDPSS RT                                   32

SEQ ID NO: 17                 moltype = AA   length = 17
FEATURE                       Location/Qualifiers
source                        1..17
                              mol_type = protein
                              note = paratuberculosis
                              organism = Mycobacterium avium
SEQUENCE: 17
KRHTQAVLAL ARRRLNV                                                    17

SEQ ID NO: 18                 moltype = AA   length = 16
FEATURE                       Location/Qualifiers
source                        1..16
                              mol_type = protein
                              note = paratuberculosis
                              organism = Mycobacterium avium
SEQUENCE: 18
KRHTQAVLAL ARRRLN                                                     16

SEQ ID NO: 19                 moltype = AA   length = 15
FEATURE                       Location/Qualifiers
source                        1..15
                              mol_type = protein
                              note = paratuberculosis
                              organism = Mycobacterium avium
SEQUENCE: 19
ELIAAVTTLA DGGEV                                                      15

SEQ ID NO: 20                 moltype = AA   length = 15
FEATURE                       Location/Qualifiers
source                        1..15
                              mol_type = protein
                              note = paratuberculosis
                              organism = Mycobacterium avium
SEQUENCE: 20
DRKRTEGKRH TQAVL                                                      15

SEQ ID NO: 21                 moltype = AA   length = 15
FEATURE                       Location/Qualifiers
source                        1..15
                              mol_type = protein
                              note = paratuberculosis
                              organism = Mycobacterium avium
SEQUENCE: 21
NKSRAALILL TGYQT                                                      15

SEQ ID NO: 22                 moltype = AA   length = 15
FEATURE                       Location/Qualifiers
source                        1..15
                              mol_type = protein
                              note = paratuberculosis
                              organism = Mycobacterium avium
SEQUENCE: 22
AKEVMALDTE IGDTD                                                      15

SEQ ID NO: 23                 moltype = AA   length = 15
FEATURE                       Location/Qualifiers
source                        1..15
                              mol_type = protein
                              note = paratuberculosis
                              organism = Mycobacterium avium
SEQUENCE: 23
ALDTEIGDTD AMIEE                                                      15

SEQ ID NO: 24                 moltype = AA   length = 40
FEATURE                       Location/Qualifiers
source                        1..40
                              mol_type = protein
                              note = paratuberculosis
                              organism = Mycobacterium avium
SEQUENCE: 24
GRISGNLKRP RRYDRRLLRA CYLSALVSIR TDPSSRTYYD                            40

SEQ ID NO: 25                 moltype = AA   length = 15
```

```
FEATURE                 Location/Qualifiers
source                  1..15
                        mol_type = protein
                        organism = Mycobacterium avium
SEQUENCE: 25
VTRLADGGEV TWAVD                                                    15

SEQ ID NO: 26           moltype = AA  length = 15
FEATURE                 Location/Qualifiers
source                  1..15
                        mol_type = protein
                        organism = Mycobacterium porcinum
SEQUENCE: 26
VATMADGGEV TWAID                                                    15

SEQ ID NO: 27           moltype = AA  length = 15
FEATURE                 Location/Qualifiers
source                  1..15
                        mol_type = protein
                        organism = Mycobacterium avium
SEQUENCE: 27
VTRLADGGEV TWAVD                                                    15

SEQ ID NO: 28           moltype = AA  length = 15
FEATURE                 Location/Qualifiers
source                  1..15
                        mol_type = protein
                        organism = Mycobacterium xenopi
SEQUENCE: 28
VTAQADGGDV TWAID                                                    15

SEQ ID NO: 29           moltype = AA  length = 15
FEATURE                 Location/Qualifiers
source                  1..15
                        mol_type = protein
                        organism = Mycobacterium porcinum
SEQUENCE: 29
NLQRPRRYNR RLLRA                                                    15

SEQ ID NO: 30           moltype = AA  length = 15
FEATURE                 Location/Qualifiers
source                  1..15
                        mol_type = protein
                        organism = Mycobacterium avium
SEQUENCE: 30
NLKRPRRYDR RLLRT                                                    15

SEQ ID NO: 31           moltype = AA  length = 15
FEATURE                 Location/Qualifiers
source                  1..15
                        mol_type = protein
                        note = silvaticum
                        organism = Mycobacterium avium
SEQUENCE: 31
NLHRPKRYNR RLRRV                                                    15

SEQ ID NO: 32           moltype = AA  length = 15
FEATURE                 Location/Qualifiers
source                  1..15
                        mol_type = protein
                        note = hominissuis
                        organism = Mycobacterium avium
SEQUENCE: 32
NLHRPKRYNR RLRRV                                                    15

SEQ ID NO: 33           moltype = AA  length = 15
FEATURE                 Location/Qualifiers
source                  1..15
                        mol_type = protein
                        organism = Leifsonia xyli
SEQUENCE: 33
NLHRPKRYDR RLLRA                                                    15

SEQ ID NO: 34           moltype = AA  length = 15
FEATURE                 Location/Qualifiers
source                  1..15
                        mol_type = protein
                        organism = Mycobacterium porcinum
SEQUENCE: 34
```

```
YLSALYSIRS DPASR                                                      15

SEQ ID NO: 35           moltype = AA   length = 15
FEATURE                 Location/Qualifiers
source                  1..15
                        mol_type = protein
                        organism = Synthetic construct
SEQUENCE: 35
YTSALVSVRY DPSSR                                                      15

SEQ ID NO: 36           moltype = AA   length = 15
FEATURE                 Location/Qualifiers
source                  1..15
                        mol_type = protein
                        organism = Mycobacterium avium
SEQUENCE: 36
YLSAQIAIRT DPASR                                                      15

SEQ ID NO: 37           moltype = AA   length = 18
FEATURE                 Location/Qualifiers
source                  1..18
                        mol_type = protein
                        note = paratuberculosis
                        organism = Mycobacterium avium
SEQUENCE: 37
VTTLADGGEV TWAIDLNA                                                   18

SEQ ID NO: 38           moltype = AA   length = 18
FEATURE                 Location/Qualifiers
source                  1..18
                        mol_type = protein
                        note = paratuberculosis
                        organism = Mycobacterium avium
SEQUENCE: 38
NKSRAALILL TGYQTPDA                                                   18

SEQ ID NO: 39           moltype = AA   length = 18
FEATURE                 Location/Qualifiers
source                  1..18
                        mol_type = protein
                        note = paratuberculosis
                        organism = Mycobacterium avium
SEQUENCE: 39
NLKRPRRYDR RLLRAGYL                                                   18

SEQ ID NO: 40           moltype = AA   length = 10
FEATURE                 Location/Qualifiers
source                  1..10
                        mol_type = protein
                        note = paratuberculosis
                        organism = Mycobacterium avium
SEQUENCE: 40
MVINDDAQRL                                                            10

SEQ ID NO: 41           moltype = AA   length = 11
FEATURE                 Location/Qualifiers
source                  1..11
                        mol_type = protein
                        note = paratuberculosis
                        organism = Mycobacterium avium
SEQUENCE: 41
MVINDDAQRL C                                                          11

SEQ ID NO: 42           moltype = AA   length = 11
FEATURE                 Location/Qualifiers
source                  1..11
                        mol_type = protein
                        note = paratuberculosis
                        organism = Mycobacterium avium
SEQUENCE: 42
CNLKRPRRYD R                                                          11

SEQ ID NO: 43           moltype = AA   length = 11
FEATURE                 Location/Qualifiers
source                  1..11
                        mol_type = protein
                        note = paratuberculosis
                        organism = Mycobacterium avium
SEQUENCE: 43
```

-continued

```
CVSIRTDPSS R                                                       11

SEQ ID NO: 44          moltype = AA  length = 15
FEATURE                Location/Qualifiers
source                 1..15
                       mol_type = protein
                       note = paratuberculosis
                       organism = Mycobacterium avium
SEQUENCE: 44
MVINDDAQRL LSQRC                                                   15

SEQ ID NO: 45          moltype = AA  length = 16
FEATURE                Location/Qualifiers
source                 1..16
                       mol_type = protein
                       note = paratuberculosis
                       organism = Mycobacterium avium
SEQUENCE: 45
VTTLADGGEV TWAIDC                                                  16

SEQ ID NO: 46          moltype = AA  length = 16
FEATURE                Location/Qualifiers
source                 1..16
                       mol_type = protein
                       note = paratuberculosis
                       organism = Mycobacterium avium
SEQUENCE: 46
YLSALVSIRT DPSSRC                                                  16

SEQ ID NO: 47          moltype = AA  length = 10
FEATURE                Location/Qualifiers
MOD_RES                1
                       note = ACETYLATION
SITE                   10
                       note = 8branchedPolylysineOctamer
source                 1..10
                       mol_type = protein
                       note = paratuberculosis
                       organism = Mycobacterium avium
SEQUENCE: 47
MVINDDAQRL                                                         10

SEQ ID NO: 48          moltype = AA  length = 10
FEATURE                Location/Qualifiers
SITE                   1
                       note = Biotinyl
MOD_RES                10
                       note = AMIDATION
source                 1..10
                       mol_type = protein
                       note = paratuberculosis
                       organism = Mycobacterium avium
SEQUENCE: 48
MVINDDAQRL                                                         10

SEQ ID NO: 49          moltype = AA  length = 9
FEATURE                Location/Qualifiers
SITE                   1
                       note = Biotinyl
MOD_RES                9
                       note = AMIDATION
source                 1..9
                       mol_type = protein
                       note = paratuberculosis
                       organism = Mycobacterium avium
SEQUENCE: 49
MVINDDLQR                                                          9

SEQ ID NO: 50          moltype = AA  length = 8
FEATURE                Location/Qualifiers
SITE                   1
                       note = Biotinyl
MOD_RES                8
                       note = AMIDATION
source                 1..8
                       mol_type = protein
                       note = paratuberculosis
                       organism = Mycobacterium avium
SEQUENCE: 50
```

```
MVINNDAE                                                                      8

SEQ ID NO: 51          moltype = AA  length = 11
FEATURE                Location/Qualifiers
MOD_RES                1
                       note = ACETYLATION
source                 1..11
                       mol_type = protein
                       note = paratuberculosis
                       organism = Mycobacterium avium
SITE                   11
                       note = 8branchedPolylysineOctamer
SEQUENCE: 51
VTTLADGGEV T                                                                 11

SEQ ID NO: 52          moltype = AA  length = 11
FEATURE                Location/Qualifiers
SITE                   1
                       note = Biotinyl
MOD_RES                11
                       note = AMIDATION
source                 1..11
                       mol_type = protein
                       note = paratuberculosis
                       organism = Mycobacterium avium
SEQUENCE: 52
VTTLADGGEV T                                                                 11

SEQ ID NO: 53          moltype = AA  length = 11
FEATURE                Location/Qualifiers
SITE                   1
                       note = Biotinyl
MOD_RES                11
                       note = AMIDATION
source                 1..11
                       mol_type = protein
                       note = paratuberculosis
                       organism = Mycobacterium avium
SEQUENCE: 53
VATMADGGEV T                                                                 11

SEQ ID NO: 54          moltype = AA  length = 11
FEATURE                Location/Qualifiers
SITE                   1
                       note = Biotinyl
MOD_RES                11
                       note = AMIDATION
source                 1..11
                       mol_type = protein
                       note = paratuberculosis
                       organism = Mycobacterium avium
SEQUENCE: 54
VTRLADGGEV T                                                                 11

SEQ ID NO: 55          moltype = AA  length = 10
FEATURE                Location/Qualifiers
MOD_RES                1
                       note = ACETYLATION
SITE                   10
                       note = 8branchedPolylysineOctamer
source                 1..10
                       mol_type = protein
                       note = paratuberculosis
                       organism = Mycobacterium avium
SEQUENCE: 55
NLKRPRRYDR                                                                   10

SEQ ID NO: 56          moltype = AA  length = 10
FEATURE                Location/Qualifiers
SITE                   1
                       note = Biotinyl
MOD_RES                10
                       note = AMIDATION
source                 1..10
                       mol_type = protein
                       note = paratuberculosis
                       organism = Mycobacterium avium
SEQUENCE: 56
NLKRPRRYDR                                                                   10
```

```
SEQ ID NO: 57          moltype = AA   length = 7
FEATURE                Location/Qualifiers
SITE                   1
                       note = Biotinyl
MOD_RES                7
                       note = AMIDATION
source                 1..7
                       mol_type = protein
                       note = paratuberculosis
                       organism = Mycobacterium avium SEQUENCE: 57
NLKRPRR                                                                    7

SEQ ID NO: 58          moltype = AA   length = 10
FEATURE                Location/Qualifiers
SITE                   1
                       note = Biotinyl
MOD_RES                10
                       note = ACETYLATION
source                 1..10
                       mol_type = protein
                       note = paratuberculosis
                       organism = Mycobacterium avium SEQUENCE: 58
NLRRPRRYHR                                                                 10

SEQ ID NO: 59          moltype = AA   length = 10
FEATURE                Location/Qualifiers
SITE                   1
                       note = Biotinyl
MOD_RES                10
                       note = AMIDATION
source                 1..10
                       mol_type = protein
                       note = paratuberculosis
                       organism = Mycobacterium avium SEQUENCE: 59
NLHRPRRYHR                                                                 10

SEQ ID NO: 60          moltype = AA   length = 10
FEATURE                Location/Qualifiers
SITE                   1
                       note = Biotinyl
MOD_RES                10
                       note = AMIDATION
source                 1..10
                       mol_type = protein
                       note = paratuberculosis
                       organism = Mycobacterium avium SEQUENCE: 60
NMRRPRRYNR                                                                 10

SEQ ID NO: 61          moltype = AA   length = 10
FEATURE                Location/Qualifiers
SITE                   1
                       note = Biotinyl
MOD_RES                10
                       note = AMIDATION
source                 1..10
                       mol_type = protein
                       note = paratuberculosis
                       organism = Mycobacterium avium SEQUENCE: 61
NLRRPKRYNR                                                                 10

SEQ ID NO: 62          moltype = AA   length = 10
FEATURE                Location/Qualifiers
SITE                   1
                       note = Biotinyl
MOD_RES                10
                       note = AMIDATION
source                 1..10
                       mol_type = protein
                       note = paratuberculosis
                       organism = Mycobacterium avium SEQUENCE: 62
NLQRPRRYNR                                                                 10
```

| | | |
|---|---|---|
| SEQ ID NO: 63<br>FEATURE<br>MOD_RES<br><br>SITE<br><br>source<br><br><br><br>SEQUENCE: 63<br>VSIRTDPSSR | moltype = AA   length = 10<br>Location/Qualifiers<br>1<br>note = ACETYLATION<br>10<br>note = 8branchedPolylysineOctamer<br>1..10<br>mol_type = protein<br>note = paratuberculosis<br>organism = Mycobacterium avium | 10 |
| SEQ ID NO: 64<br>FEATURE<br>SITE<br><br>MOD_RES<br><br>source<br><br><br><br>SEQUENCE: 64<br>VSIRTDPSSR | moltype = AA   length = 10<br>Location/Qualifiers<br>1<br>note = Biotinyl<br>10<br>note = AMIDATION<br>1..10<br>mol_type = protein<br>note = paratuberculosis<br>organism = Mycobacterium avium | 10 |
| SEQ ID NO: 65<br>FEATURE<br>SITE<br><br>MOD_RES<br><br>source<br><br><br><br>SEQUENCE: 65<br>VSIRTDP | moltype = AA   length = 7<br>Location/Qualifiers<br>1<br>note = Biotinyl<br>7<br>note = AMIDATION<br>1..7<br>mol_type = protein<br>note = paratuberculosis<br>organism = Mycobacterium avium | 7 |
| SEQ ID NO: 66<br>FEATURE<br>SITE<br><br>MOD_RES<br><br>source<br><br><br><br>SEQUENCE: 66<br>SIRSDPSSR | moltype = AA   length = 9<br>Location/Qualifiers<br>1<br>note = Biotinyl<br>9<br>note = AMIDATION<br>1..9<br>mol_type = protein<br>note = paratuberculosis<br>organism = Mycobacterium avium | 9 |
| SEQ ID NO: 67<br>FEATURE<br>SITE<br><br>MOD_RES<br><br>source<br><br><br><br>SEQUENCE: 67<br>YSIRSDPASR | moltype = AA   length = 10<br>Location/Qualifiers<br>1<br>note = Biotinyl<br>10<br>note = AMIDATION<br>1..10<br>mol_type = protein<br>note = paratuberculosis<br>organism = Mycobacterium avium | 10 |
| SEQ ID NO: 68<br>FEATURE<br>SITE<br><br>MOD_RES<br><br>source<br><br><br><br>SEQUENCE: 68<br>VSVRYDPSSR | moltype = AA   length = 10<br>Location/Qualifiers<br>1<br>note = Biotinyl<br>10<br>note = AMIDATION<br>1..10<br>mol_type = protein<br>note = paratuberculosis<br>organism = Mycobacterium avium | 10 |
| SEQ ID NO: 69 | moltype = AA   length = 10 | |

```
FEATURE                 Location/Qualifiers
SITE                    1
                        note = Biotinyl
MOD_RES                 10
                        note = AMIDATION
source                  1..10
                        mol_type = protein
                        note = paratuberculosis
                        organism = Mycobacterium avium SEQUENCE: 69
IAIRTDPASR                                                              10

SEQ ID NO: 70           moltype = AA  length = 11
FEATURE                 Location/Qualifiers
MOD_RES                 1
                        note = ACETYLATION
source                  1..11
                        mol_type = protein
                        note = paratuberculosis
                        organism = Mycobacterium avium SEQUENCE: 70
MVINDDAQRL C                                                            11

SEQ ID NO: 71           moltype = AA  length = 12
FEATURE                 Location/Qualifiers
MOD_RES                 1
                        note = ACETYLATION
source                  1..12
                        mol_type = protein
                        note = paratuberculosis
                        organism = Mycobacterium avium SEQUENCE: 71
VTTLADGGEV TC                                                           12

SEQ ID NO: 72           moltype = AA  length = 11
FEATURE                 Location/Qualifiers
MOD_RES                 1
                        note = ACETYLATION
source                  1..11
                        mol_type = protein
                        note = paratuberculosis
                        organism = Mycobacterium avium SEQUENCE: 72
NLKRPRRYDR C                                                            11

SEQ ID NO: 73           moltype = AA  length = 11
FEATURE                 Location/Qualifiers
MOD_RES                 1
                        note = ACETYLATION
source                  1..11
                        mol_type = protein
                        note = paratuberculosis
                        organism = Mycobacterium avium SEQUENCE: 73
VSIRTDPSSR C                                                            11

SEQ ID NO: 74           moltype = AA  length = 15
FEATURE                 Location/Qualifiers
MOD_RES                 15
                        note = AMIDATION
source                  1..15
                        mol_type = protein
                        note = paratuberculosis
                        organism = Mycobacterium avium SEQUENCE: 74
CMVINDDAQR LLSQR                                                        15

SEQ ID NO: 75           moltype = AA  length = 14
FEATURE                 Location/Qualifiers
SITE                    1
                        note = Biotinyl
MOD_RES                 14
                        note = AMIDATION
source                  1..14
                        mol_type = protein
                        note = paratuberculosis
                        organism = Mycobacterium avium SEQUENCE: 75
MVINDDAQRL LSQR                                                         14
```

```
SEQ ID NO: 76              moltype = AA  length = 14
FEATURE                    Location/Qualifiers
SITE                       1
                           note = Biotinyl
MOD_RES                    14
                           note = AMIDATION
source                     1..14
                           mol_type = protein
                           note = paratuberculosis
                           organism = Mycobacterium avium
SEQUENCE: 76
MVINDDLQRI ILFL                                                        14

SEQ ID NO: 77              moltype = AA  length = 14
FEATURE                    Location/Qualifiers
SITE                       1
                           note = Biotinyl
MOD_RES                    14
                           note = AMIDATION
source                     1..14
                           mol_type = protein
                           note = paratuberculosis
                           organism = Mycobacterium avium
SEQUENCE: 77
MSINDDAQKL KDRL                                                        14

SEQ ID NO: 78              moltype = AA  length = 15
FEATURE                    Location/Qualifiers
MOD_RES                    13
                           note = PHOSPHORYLATION
SITE                       15
                           note = Amide BSA conjugated
source                     1..15
                           mol_type = protein
                           note = paratuberculosis
                           organism = Mycobacterium avium
SEQUENCE: 78
CMVINDDAQR LLSQR                                                       15

SEQ ID NO: 79              moltype = AA  length = 14
FEATURE                    Location/Qualifiers
SITE                       1
                           note = Biotinyl
MOD_RES                    12
                           note = PHOSPHORYLATION
MOD_RES                    14
                           note = AMIDATION
source                     1..14
                           mol_type = protein
                           note = paratuberculosis
                           organism = Mycobacterium avium
SEQUENCE: 79
MVINDDAQRL LSQR                                                        14

SEQ ID NO: 80              moltype = AA  length = 14
FEATURE                    Location/Qualifiers
SITE                       1
                           note = Biotinyl
MOD_RES                    14
                           note = AMIDATION
source                     1..14
                           mol_type = protein
                           note = paratuberculosis
                           organism = Mycobacterium avium
SEQUENCE: 80
MVINDDAQRL LSQR                                                        14

SEQ ID NO: 81              moltype = AA  length = 21
FEATURE                    Location/Qualifiers
MOD_RES                    1
                           note = ACETYLATION
SITE                       21
                           note = BSA conjugated
source                     1..21
                           mol_type = protein
                           note = paratuberculosis
                           organism = Mycobacterium avium
SEQUENCE: 81
```

```
AAVTTLADGG EVTWAIDGKK C                                                         21

SEQ ID NO: 82           moltype = AA  length = 20
FEATURE                 Location/Qualifiers
SITE                    1
                        note = Biotinyl
MOD_RES                 20
                        note = AMIDATION
source                  1..20
                        mol_type = protein
                        note = paratuberculosis
                        organism = Mycobacterium avium
SEQUENCE: 82
KKGAAVTTLA DGGEVTWAID                                                           20

SEQ ID NO: 83           moltype = AA  length = 20
FEATURE                 Location/Qualifiers
SITE                    1
                        note = Biotinyl
MOD_RES                 20
                        note = AMIDATION
source                  1..20
                        mol_type = protein
                        note = paratuberculosis
                        organism = Mycobacterium avium
SEQUENCE: 83
KKGAAGTTLA DGGEVTWAID                                                           20

SEQ ID NO: 84           moltype = AA  length = 20
FEATURE                 Location/Qualifiers
SITE                    1
                        note = Biotinyl
MOD_RES                 20
                        note = AMIDATION
source                  1..20
                        mol_type = protein
                        note = paratuberculosis
                        organism = Mycobacterium avium
SEQUENCE: 84
KKGSTVATMA DGGEVTWAID                                                           20

SEQ ID NO: 85           moltype = AA  length = 20
FEATURE                 Location/Qualifiers
SITE                    1
                        note = Biotinyl
MOD_RES                 20
                        note = AMIDATION
source                  1..20
                        mol_type = protein
                        note = paratuberculosis
                        organism = Mycobacterium avium
SEQUENCE: 85
KKGQAVTRLA DGGEVTWAVD                                                           20

SEQ ID NO: 86           moltype = AA  length = 20
FEATURE                 Location/Qualifiers
SITE                    1
                        note = Biotinyl
MOD_RES                 20
                        note = AMIDATION
source                  1..20
                        mol_type = protein
                        note = paratuberculosis
                        organism = Mycobacterium avium
SEQUENCE: 86
KKGFEVTTLA DGTEVATSPL                                                           20

SEQ ID NO: 87           moltype = AA  length = 16
FEATURE                 Location/Qualifiers
MOD_RES                 15
                        note = PHOSPHORYLATION
SITE                    16
                        note = Amide BSA conjugated
source                  1..16
                        mol_type = protein
                        note = paratuberculosis
                        organism = Mycobacterium avium
SEQUENCE: 87
CYLSALVSIR TDPSSR                                                               16
```

```
SEQ ID NO: 88            moltype = AA   length = 15
FEATURE                  Location/Qualifiers
SITE                     1
                         note = Biotinyl
MOD_RES                  14
                         note = PHOSPHORYLATION
MOD_RES                  15
                         note = AMIDATION
source                   1..15
                         mol_type = protein
                         note = paratuberculosis
                         organism = Mycobacterium avium
SEQUENCE: 88
YLSALVSIRT DPSSR                                                            15

SEQ ID NO: 89            moltype = AA   length = 15
FEATURE                  Location/Qualifiers
SITE                     1
                         note = Biotinyl
MOD_RES                  15
                         note = AMIDATION
source                   1..15
                         mol_type = protein
                         note = paratuberculosis
                         organism = Mycobacterium avium
SEQUENCE: 89
YLSALVSIRT DPSSR                                                            15

SEQ ID NO: 90            moltype = AA   length = 15
FEATURE                  Location/Qualifiers
SITE                     1
                         note = Biotinyl
MOD_RES                  14
                         note = PHOSPHORYLATION
MOD_RES                  15
                         note = AMIDATION
source                   1..15
                         mol_type = protein
                         note = paratuberculosis
                         organism = Mycobacterium avium
SEQUENCE: 90
YLSALYSIRS DPASR                                                            15

SEQ ID NO: 91            moltype = AA   length = 15
FEATURE                  Location/Qualifiers
SITE                     1
                         note = Biotinyl
MOD_RES                  14
                         note = PHOSPHORYLATION
MOD_RES                  15
                         note = AMIDATION
source                   1..15
                         mol_type = protein
                         note = paratuberculosis
                         organism = Mycobacterium avium
SEQUENCE: 91
YLSALVSVRY DPSSR                                                            15

SEQ ID NO: 92            moltype = AA   length = 15
FEATURE                  Location/Qualifiers
SITE                     1
                         note = Biotinyl
MOD_RES                  14
                         note = PHOSPHORYLATION
MOD_RES                  15
                         note = AMIDATION
source                   1..15
                         mol_type = protein
                         note = paratuberculosis
                         organism = Mycobacterium avium
SEQUENCE: 92
YLSAQIAIRT DPASR                                                            15

SEQ ID NO: 93            moltype = AA   length = 14
FEATURE                  Location/Qualifiers
SITE                     1
                         note = BSA
MOD_RES                  14
```

```
                    note = AMIDATION
source              1..14
                    mol_type = protein
                    note = paratuberculosis
                    organism = Mycobacterium avium
SEQUENCE: 93
MVINDDAQRL LSQR                                                          14

SEQ ID NO: 94       moltype = AA  length = 14
FEATURE             Location/Qualifiers
SITE                1
                    note = BSA
MOD_RES             12
                    note = PHOSPHORYLATION
source              1..14
                    mol_type = protein
                    note = paratuberculosis
                    organism = Mycobacterium avium
SEQUENCE: 94
MVINDDAQRL LSQR                                                          14

SEQ ID NO: 95       moltype = AA  length = 10
FEATURE             Location/Qualifiers
SITE                1
                    note = BSA
MOD_RES             10
                    note = AMIDATION
source              1..10
                    mol_type = protein
                    note = paratuberculosis
                    organism = Mycobacterium avium
SEQUENCE: 95
VSIRTDPSSR                                                               10

SEQ ID NO: 96       moltype = AA  length = 15
FEATURE             Location/Qualifiers
SITE                1
                    note = BSA
MOD_RES             14
                    note = PHOSPHORYLATION
MOD_RES             15
                    note = AMIDATION
source              1..15
                    mol_type = protein
                    note = paratuberculosis
                    organism = Mycobacterium avium
SEQUENCE: 96
YLSALVSIRT DPSSR                                                         15

SEQ ID NO: 97       moltype = AA  length = 16
FEATURE             Location/Qualifiers
SITE                1
                    note = Biotinyl
MOD_RES             15
                    note = PHOSPHORYLATION
source              1..16
                    mol_type = protein
                    note = paratuberculosis
                    organism = Mycobacterium avium
SEQUENCE: 97
YLSALVSVRY DPSPSR                                                        16

SEQ ID NO: 98       moltype = AA  length = 11
FEATURE             Location/Qualifiers
source              1..11
                    mol_type = protein
                    note = paratuberculosis
                    organism = Mycobacterium avium
MOD_RES             10
                    note = PHOSPHORYLATION
SEQUENCE: 98
VSIRTDPSPS R                                                             11
```

METHOD OF DETECTING *MYCOBACTERIUM AVIUM* SUBSPECIES PARATUBERCULOSIS INFECTION

CROSS-REFERENCE TO RELATED APPLICATIONS

This application is a continuation application of U.S. patent application Ser. No. 17/348,428, filed Jun. 15, 2021, now U.S. Pat. No. 11,714,085, which is a continuation of U.S. patent application Ser. No. 16/476,656, filed Jul. 9, 2019, now abandoned, which is a national stage application under 35 U.S.C. 371 and claims the benefit of PCT Application No. PCT/GB2018/050075 having an international filing date of 11 Jan. 2018, which designated the United States, which PCT application claimed the benefit of Great Britain Patent Application No. 1700487.0 filed 11 Jan. 2017, the disclosures of each of which are incorporated herein by reference in their entireties.

REFERENCE TO SEQUENCE LISTING

This application contains a Sequence Listing submitted as an electronic XML file named "Sequence_Listing_in_ST26_N407615US_B_PXT_KZX.xml", having a size in bytes of 140000 bytes, and created on 10 Aug. 2023. The information contained in this electronic file is hereby incorporated by reference in its entirety pursuant to 37 CFR § 1.52(e)(5).

FIELD OF THE INVENTION

The present invention relates to the detection of *Mycobacterium avium* subspecies paratuberculosis (MAP). In particular the invention relates to diagnosis, monitoring and treatment of MAP infection, and of disorders associated with such infection. The invention provides antibodies that bind specifically to MAP proteins and peptide fragments specific to MAP and to uses of those antibodies and peptide fragments.

BACKGROUND TO THE INVENTION

*Mycobacterium avium* subspecies paratuberculosis (MAP) is a mycobacterial pathogen that is a member of the *Mycobacterium avium* complex (MAC). Unlike other environmental MAC, MAP has the specific ability to cause chronic inflammation of the intestine of a range of histopathological types in many animals including primates.

MAP was first reported from Germany in 1895 as the cause of chronic inflammation of the intestine in a dairy cow. The condition came to be called Johne's disease (JD). During the first half of the 20$^{th}$ century JD principally affected Europe and North America but it has since spread worldwide to become a global problem.

MAP infection in the absence of apparent clinical JD can persist in livestock for years during which time they shed MAP into their milk and onto pastures. Run-off from pastures contaminates rivers and surface waters from which humans may be exposed in aerosols and domestic water supplies. Human populations may also be exposed to residual viable MAP in milk from which its elimination by pasteurisation is not assured. The presence of residual live MAP has recently been confirmed in infant powered milk (Botsaris et al. "Detection of viable *Mycobacterium avium* subspecies paratuberculosis in powdered infant formula by phage-PCR and confirmed by culture" International Journal of Food Microbiology 2016; 216: 91-94). MAP is now known to be able to infect and cause chronic inflammation of the intestine in many species including primates. Its involvement in the causation of Crohn's disease (CD) in humans has long been suspected but despite increasing evidence, this major public health uncertainty has never been resolved (Hermon-Taylor. "*Mycobacterium avium* subspecies paratuberculosis, Crohn's Disease and the Doomsday Scenario" Gut Pathogens 2009; 1:15).

MAP has not so far been seen in diseased tissues in Crohn's disease and at present there is no practically applicable clinical diagnostic test for MAP infection in human medicine. In humans the lack of a practically applicable clinical diagnostic is a major unmet medical need (Nacy and Buckey, "*Mycobacterium avium* paratuberculosis: Infrequent Human Pathogen or Public Health Threat? A Report from the American Academy of Microbiology" 2008). Furthermore the MAP diagnostics available for animals are not good at the early detection of low grade subclinical infection.

SUMMARY OF THE INVENTION

The present inventor has developed a sensitive and reliable method for detecting *Mycobacterium avium* subspecies paratuberculosis (MAP). The inventor has developed antibodies that are highly specific to MAP and that recognise regions of MAP that are exposed on the surface of MAP and within and on the surface of MAP infected host cells. The antibodies bind to the polypeptide encoded by the positive strand of MAP IS900. Using the antibodies, the inventor has shown that MAP is widely present in samples from patients with Crohn's disease but also other diseases and conditions including Psoriasis, Hashimoto's Thyroiditis, Irritable Bowel Syndrome and others (Scanu et al. "*Mycobacterium avium* Subspecies paratuberculosis Infection in Cases of Irritable Bowel Syndrome and Comparison with Crohn's Disease and Johne's disease: Common Neural and Immune Pathogenicities" Journal Clinical Microbiology. 2007; 45: 3883-3890). The inventor has detected MAP, not only in tissue samples from the affected regions, but also in bodily fluids including blood and breast milk. The inventor has shown that the antibodies may be used to detect MAP organisms, cells infected with MAP and cleaved MAP polypeptide fragments.

Furthermore, the inventor has developed antibodies that are specific either for a non-phosphorylated sequence within the polypeptide encoded by the positive strand of MAP IS900 or for the same sequences after phosphorylation, i.e. the antibodies are mutually exclusive. Using these non-phosphorylation and phosphorylation specific antibodies, the inventor has found that the phosphorylation status may be used to determine the status of the MAP infection. He has also found that non-phosphorylation and phosphorylation specific antibodies may be used in combination to characterise the level and activity of the MAP infection.

The inventor has identified peptide fragments of the MAP P900 polypeptide that have maximum specificity for MAP and that are immunogenic. The selection of the target amino acid sequences from within the accessible extracellular amino terminal and carboxy terminal portions of the MAP P900 polypeptide is principally governed by their specificity for the MAP pathogen so that the diagnostic antibodies to them do not cross react with closely related sequences.

Accordingly, the present invention provides a method of diagnosing or monitoring *Mycobacterium avium* subspecies paratuberculosis (MAP) infection, which method comprises detecting the presence of the polypeptide (MAP P900) encoded by the positive strand of IS900 (MAP IS900), or a fragment thereof, in a sample from a subject, wherein MAP P900, or a fragment thereof, is detected using an antibody, or an antigen-binding fragment thereof, that binds to MAP P900.

The antibody, or antigen-binding fragment thereof, preferably binds the region of MAP P900 defined by amino acids 24 to 71 or 329 to 386 of SEQ ID NO: 1. Preferred antibodies, or antigen-binding fragments thereof, binds the region of MAP P900 defined by:
- amino acids 26 to 71 of SEQ ID NO: 1;
- amino acids or 329 to 385 of SEQ ID NO: 1;
- amino acids 26 to 39 of SEQ ID NO: 1;
- amino acids or 52 to 68 of SEQ ID NO: 1;
- amino acids or 345 to 359 or 350 to 359 of SEQ ID NO: 1;
- amino acids 26 to 71 of SEQ ID NO: 1, wherein serine 37 is phosphorylated;
- amino acids or 345 to 359 or 350 to 359 of SEQ ID NO: 1, wherein serine 357 is phosphorylated and/or serine 358 is phosphorylated.

The method of the invention may utilise two or more of said antibodies, or antigen-binding fragments thereof, to detect MAP P900. For example, the method may utilise:
- at least one antibody that binds to the region of MAP P900 defined by amino acids 26 to 71 of SEQ ID NO: 1 and at least one further antibody that binds to the region of MAP P900 defined by amino acids or 329 to 385 of SEQ ID NO: 1;
- at least one antibody that binds to the region of MAP P900 defined by amino acids 26 to 39 of SEQ ID NO: 1 and at least one further antibody that binds to the region of MAP P900 defined by amino acids or 52 to 68 of SEQ ID NO: 1;
- at least one antibody that binds to the region of MAP P900 defined by amino acids 52 to 68 of SEQ ID NO: 1 and at least one further antibody that binds to the region of MAP P900 defined by amino acids or 345 to 359 or 350 to 359 of SEQ ID NO: 1;
- at least one antibody that binds to the region of MAP P900 defined by amino acids 26 to 71 of SEQ ID NO: 1, wherein serine 37 is optionally phosphorylated and at least one further antibody that binds to the region of MAP P900 defined by amino acids or 345 to 359 or 350 to 359 of SEQ ID NO: 1, wherein serine 357 and/or serine 358 is optionally phosphorylated.

In one embodiment, the method of the invention comprises determining whether the region of MAP P900 between amino acids 273 to 406 of SEQ ID NO: 1, or a fragment of either thereof, has been cleaved from membrane-bound MAP P900 and optionally whether the cleaved region of MAP P900, or fragment thereof, has spread from microbial cells and/or host cells containing membrane bound MAP P900.

In one embodiment, the method of the invention uses at least one antibody that specifically binds to a non-phosphorylated MAP P900 sequence and at least one further antibody that specifically binds to phosphorylated MAP P900 sequence. Preferably, the non-phosphorylated MAP P900 sequence is MVINDDAQRLLSQR (SEQ ID NO:2), and the phosphorylated MAP P900 sequence is MVINDDAQRLL[pS]QR (SEQ ID NO:3), or the non-phosphorylated MAP P900 sequence is YLSALVSIRTDPSSR (SEQ ID NO:4) or VSIRTDPSSR (SEQ ID NO:5), and the phosphorylated MAP P900 sequence is YLSALVSIRTDPS[pS]R (SEQ ID NO:6), YLSALVSIRTDP[pS]SR (SEQ ID NO:7), YLSALVSIRTDP[pS][pS]R (SEQ ID NO:13), VSIRTDPS[pS]R (SEQ ID NO:98), VSIRTDP[pS]SR (SEQ ID NO:9) or VSIRTDP[pS][pS]R (SEQ ID NO:8).

The sample is preferably a sample of a body fluid or a tissue sample. The body fluid may be, for example, blood, semen, amniotic fluid, cerebrospinal fluid, synovial fluid or breast milk, or the tissue may be, for example, skin, muscle, gastrointestinal tract, thyroid, lymph node, brain or genitourinary tract.

The subject preferably has Crohn's disease, psoriasis, thyroiditis, Parkinson's disease, type 1 diabetes, arthritis, ankylosing spondylitis, irritable bowel syndrome, ulcerative colitis, inflammatory bowel disease, Alzheimer's disease, multiple sclerosis, sarcoidosis, idiopathic pulmonary fibrosis and/or chronic fatigue syndrome.

The invention also provides:
- An antibody, or antigen-binding fragment thereof, which specifically binds to the region of MAP P900 defined by amino acids 26 to 71 of SEQ ID NO: 1, preferably an antibody, or antigen-binding fragment thereof, that binds to the amino acid sequence MVINDDAQRLLSQR (SEQ ID NO:2), AAVTTLADGGEVTWAID (SEQ ID NO: 10) or MVINDDAQRLL[pS]QR (SEQ ID NO: 3);
- An antibody, or antigen-binding fragment thereof, which specifically binds to a phosphorylated sequence within the region of MAP P900 defined by amino acids 26 to 71 or 345 to 371 of SEQ ID NO: 1; preferably an antibody, or antigen-binding fragment thereof, that binds to the sequence MVINDDAQRLLSQR (SEQ ID NO:2) or YLSALVSIRTDPSSR (SEQ ID NO:4), when one or more of the serine residues is phosphorylated;
- An antibody, or antigen-binding fragment thereof, that specifically binds to the amino acid sequence YLSALVSIRTDPSSR (SEQ ID NO:4) or NLKRPRRYDRRLLRA (SEQ ID NO:11) or a phosphorylated form of either thereof, within the region of MAP P900 defined by amino acids 329 to 360 of SEQ ID NO: 1;
- Use of an antibody, or antigen-binding fragment thereof, as defined herein in an ex vivo method of diagnosing or monitoring MAP infection;
- Use of an antibody, or antigen-binding fragment thereof, as defined herein in an ex vivo method of monitoring treatment of MAP infection, or treatment of a subject having Crohn's disease, Ulcerative Colitis, Psoriasis, Thyroiditis, Sarcoidosis, Parkinson's disease, Multiple Sclerosis, Type 1 Diabetes, arthritis, ankylosing spondylitis and irritable bowel syndrome, inflammatory bowel disease, Alzheimer's disease, multiple sclerosis, idiopathic pulmonary fibrosis and/or chronic fatigue syndrome;
- Use of an antibody, or antigen-binding fragment thereof, as defined herein to detect MAP in a food product, such as milk, another diary product or a meat product;
- Use of an antibody, or antigen-binding fragment thereof as defined herein in a method for detecting MAP in an environmental sample, such as a sample of surface water, river water, water-treatment plant water, domestic water, or an aerosol, soil or sediment;
- Use of an antibody, or antigen-binding fragment thereof, as defined herein to capture a peptide for Mass Spectrometry (MS) or Mass Cytometry characterisation;
- A peptide fragment of MAP P900 of up to 40 amino acids comprising one or more of the following sequences: MVINDDAQRLLSQR (SEQ ID NO:2), VTTLADGGEVTWAID (SEQ ID NO:12), NLKRPRRYDRRLLRA (SEQ ID NO:11), VSIRTDPSSR (SEQ ID NO:5) and YLSALVSIRTDPSSR (SEQ ID NO:4), wherein the peptide is optionally phosphorylated, wherein the phosphorylated peptide preferably comprises one of the following sequences: MVINDDAQRLL[pS]QR (SEQ ID NO: 3) or YLSALVSIRTDPS[pS]R (SEQ ID NO:6), YLSALVSIRTDP[pS]SR (SEQ ID NO:7) or YLSALVSIRTDP[pS][pS]R (SEQ ID NO:13);

A method of generating an antibody that specifically binds to MAP P900, which method comprises administering a peptide as defined herein to a laboratory animal to generate an immune response and isolating antibodies from the animal;

An antibody, or antigen-binding fragment thereof, as defined herein for use in therapeutic or diagnostic method carried out on the human or animal body An antibody, or antigen-binding fragment thereof, as defined herein for use in a method of treating or preventing MAP infection.

BRIEF DESCRIPTION OF THE SEQUENCE LISTING

Figure 1:
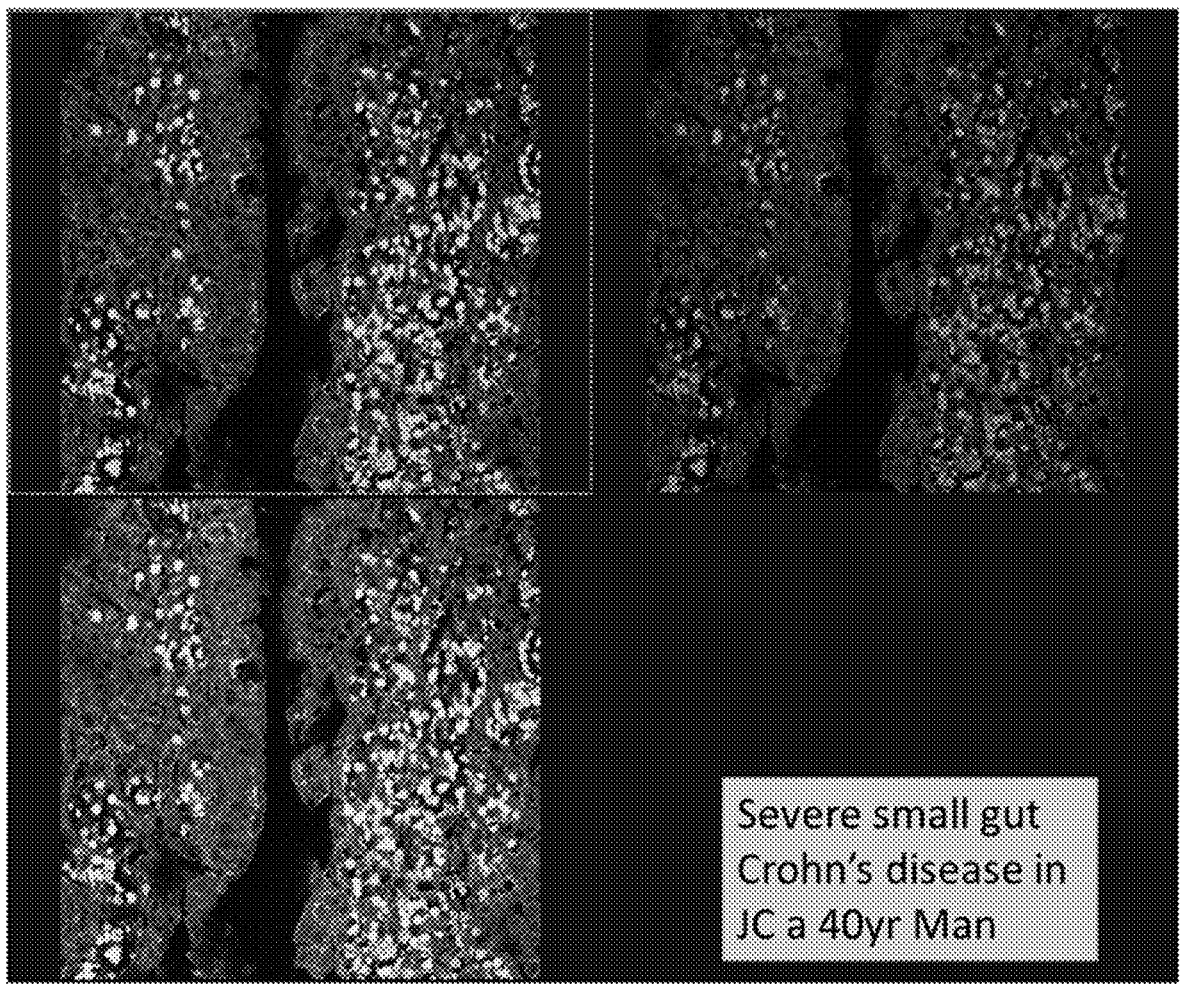
FIG. 1 shows the staining of MAP ISP900 in the ileum in a 40 year old man with Crohn's disease using two specific monoclonal antibodies against *Mycobacterium avium* subspecies paratuberculosis (MAP). These are A1 in red (top right) and A4 in green (top left). The bottom panel shows the two together.
Figure 2:
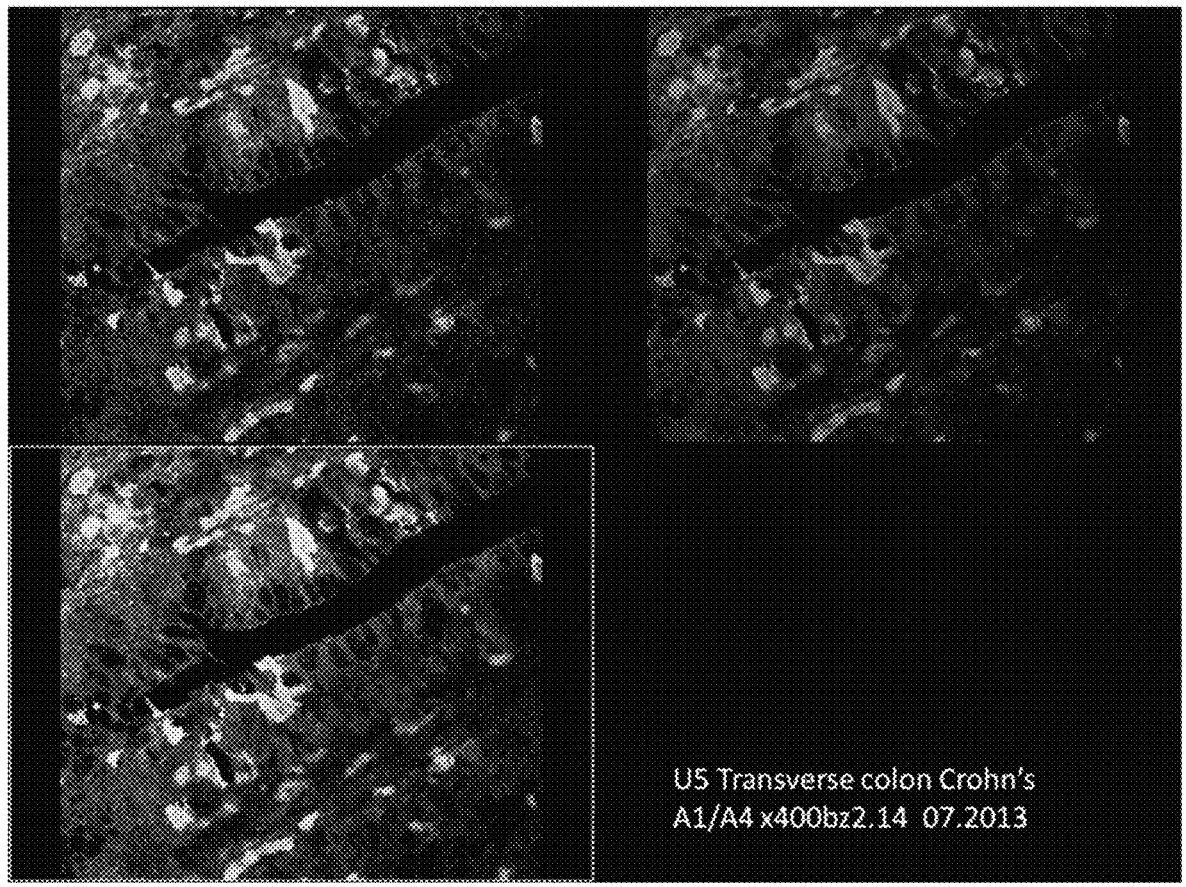
FIG. 2 shows the transverse colon of an individual with Crohn's disease stained using the A1 (red/top right) and A4 antibodies (green/top left). The bottom panel shows the two together.
Figure 3:
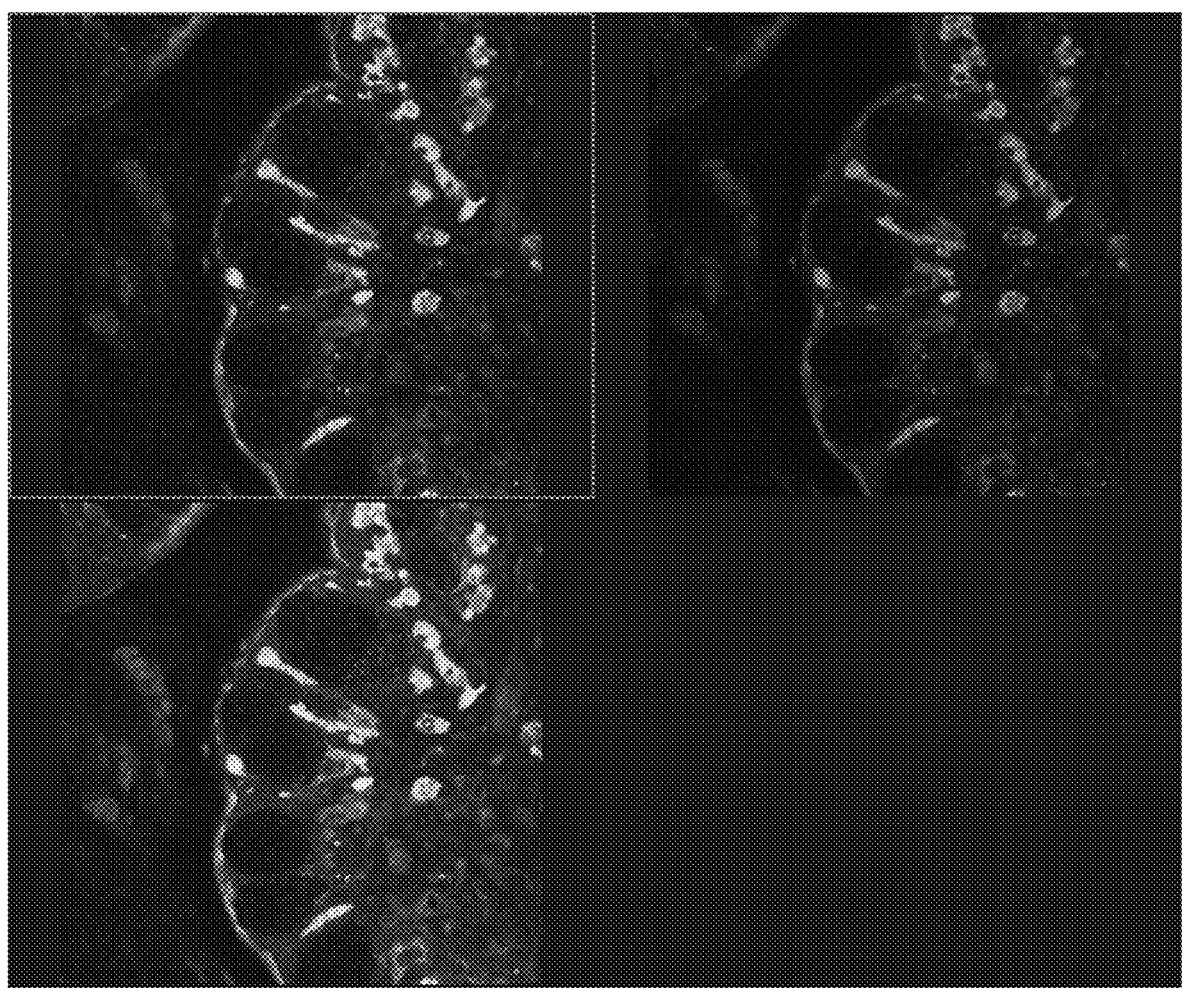
FIG. 3 shows the ileum of an individual with Crohn's disease stained using the A1 (red/top right) and A4 antibodies (green/top left). The bottom panel shows the two together.
Figure 4:
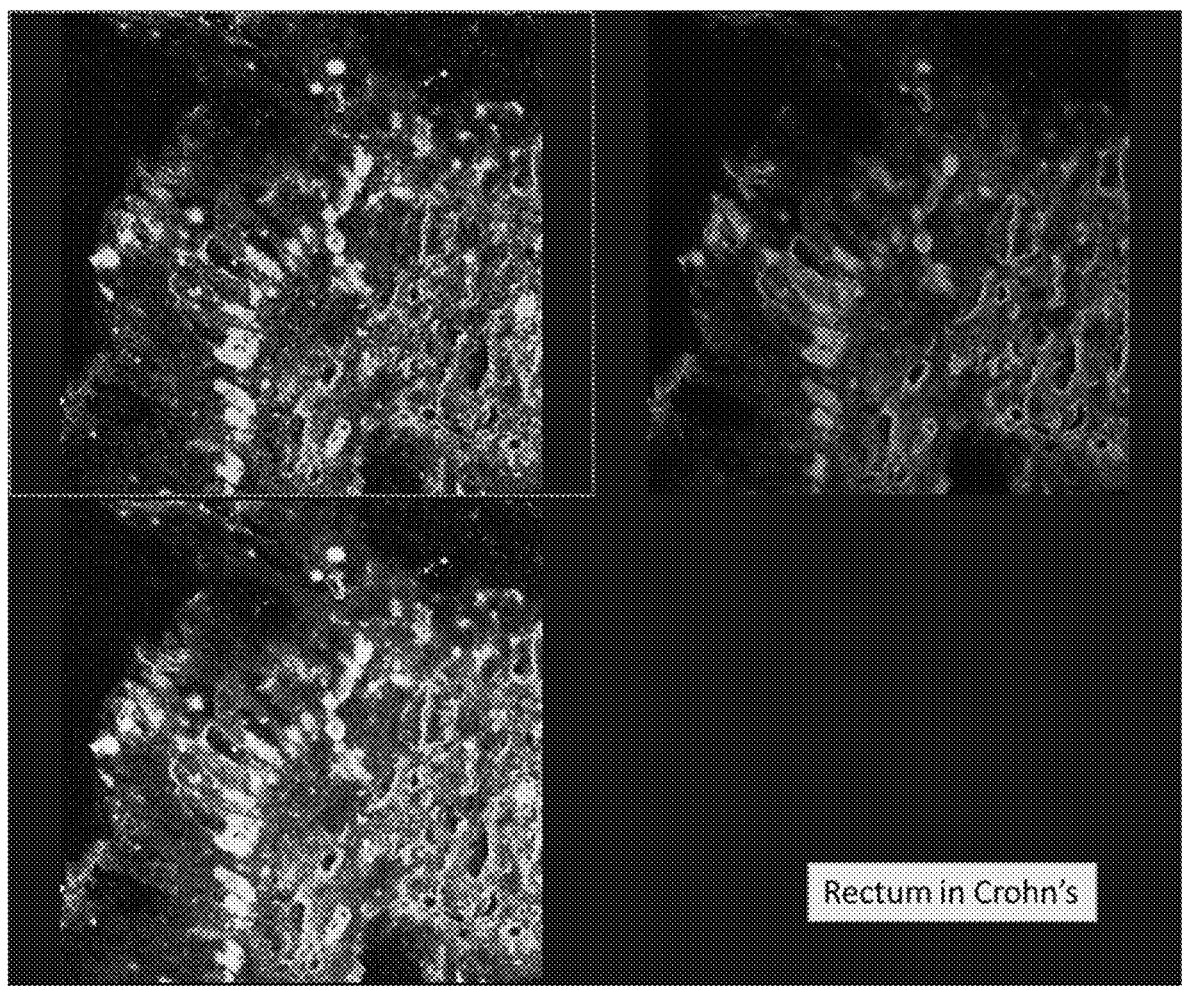
FIG. 4 shows the rectum of a 3 month old male child with Crohn's disease stained using the A1 (red/top right) and A4 antibodies (green/top left). The bottom panel shows the two together.
Figure 5:
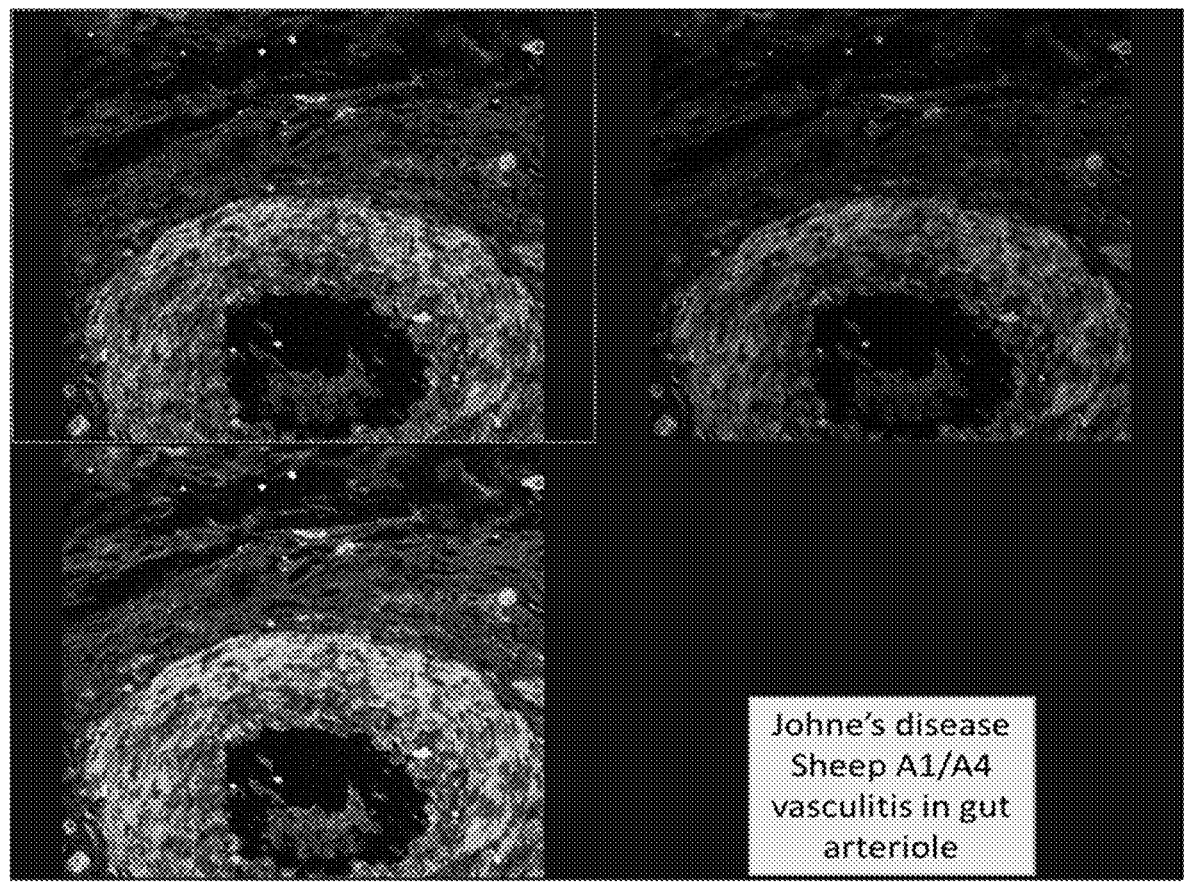
FIG. 5 shows a gut arteriole in a sheep with Johne's disease stained using the A1 (red/top right) and A4 antibodies (green/top left). The bottom panel shows the two together.
Figure 6:
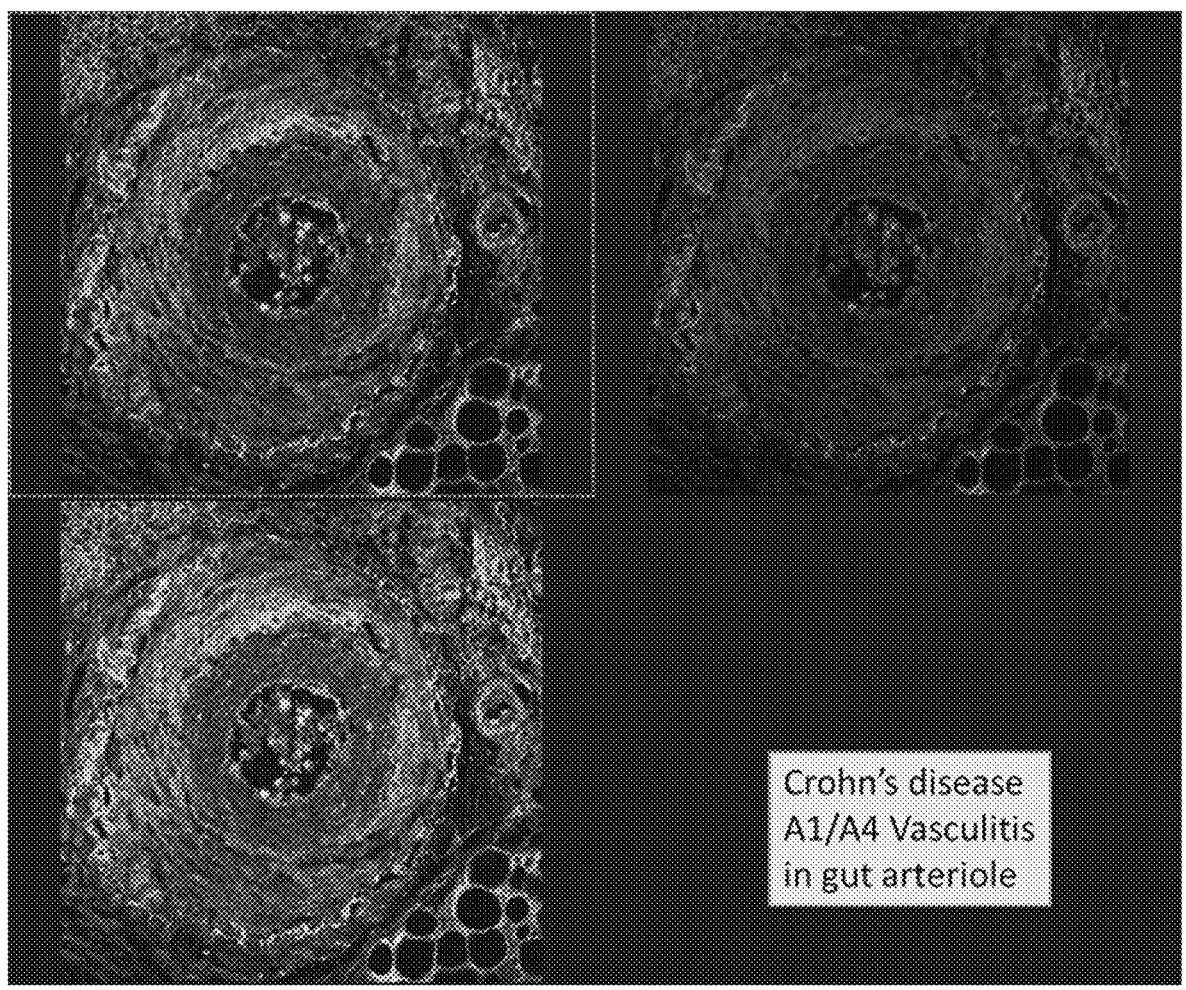
FIG. 6 shows a gut arteriole in a an individual with Crohn's disease stained using the A1 (red/top right) and A4 antibodies (green/top left). The bottom panel shows the two together.
Figure 7:
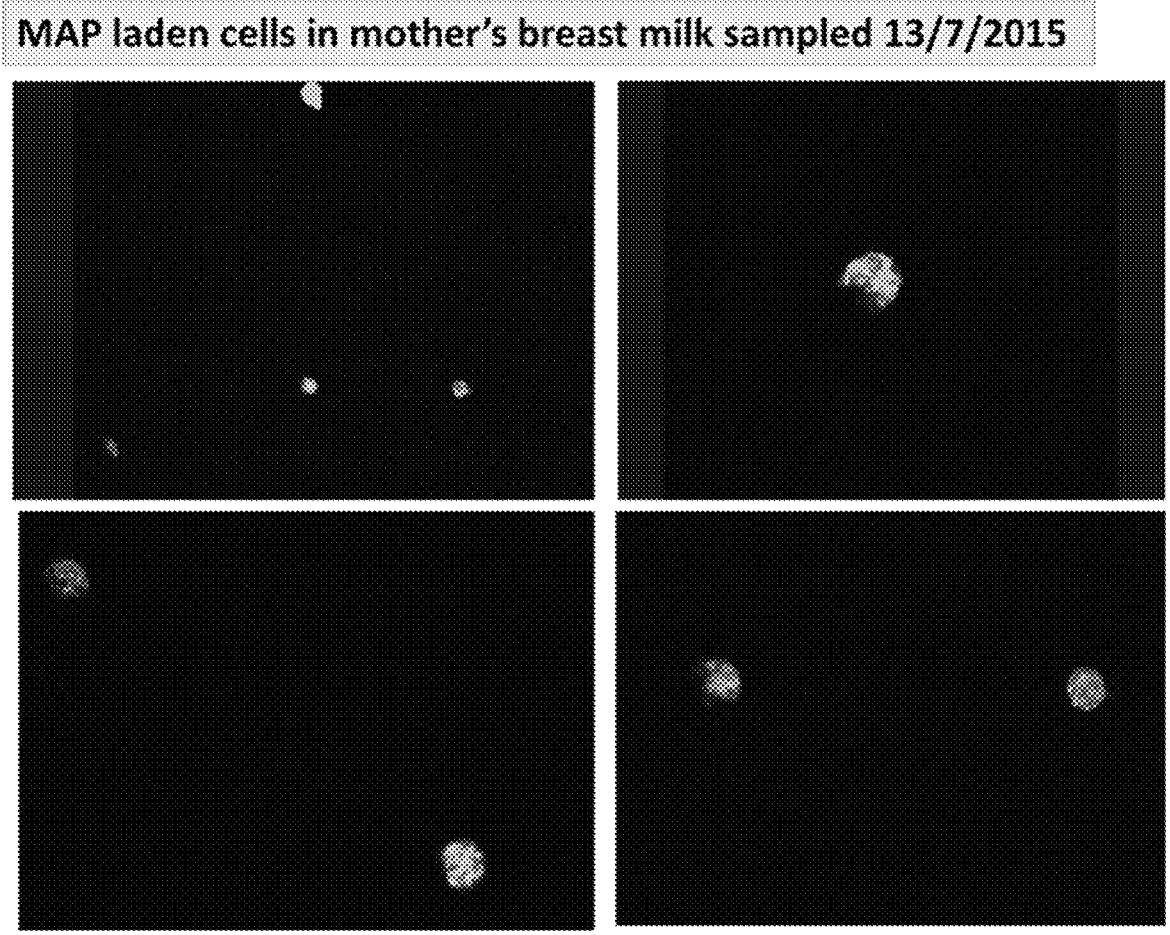
FIG. 7 shows MAP-laden white blood cells in breast milk stained using the A0X antibody.
Figure 8:
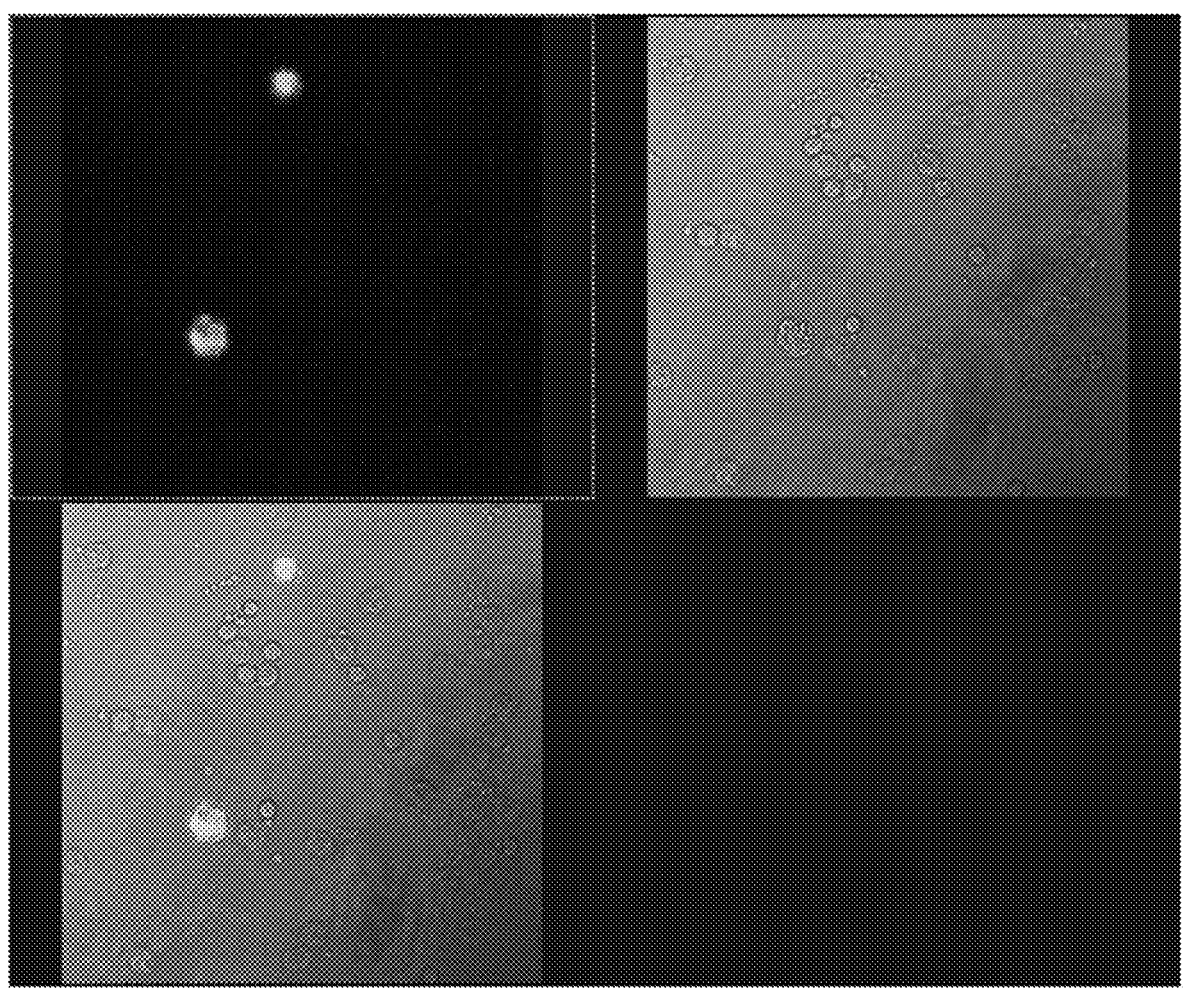
FIG. 8 shows MAP-Laden white blood cells in blood. A phase contrast image of the cells is shown (top right) and staining with the A0X antibody (top left). The bottom panel is an overlay of the two images.
Figure 9:
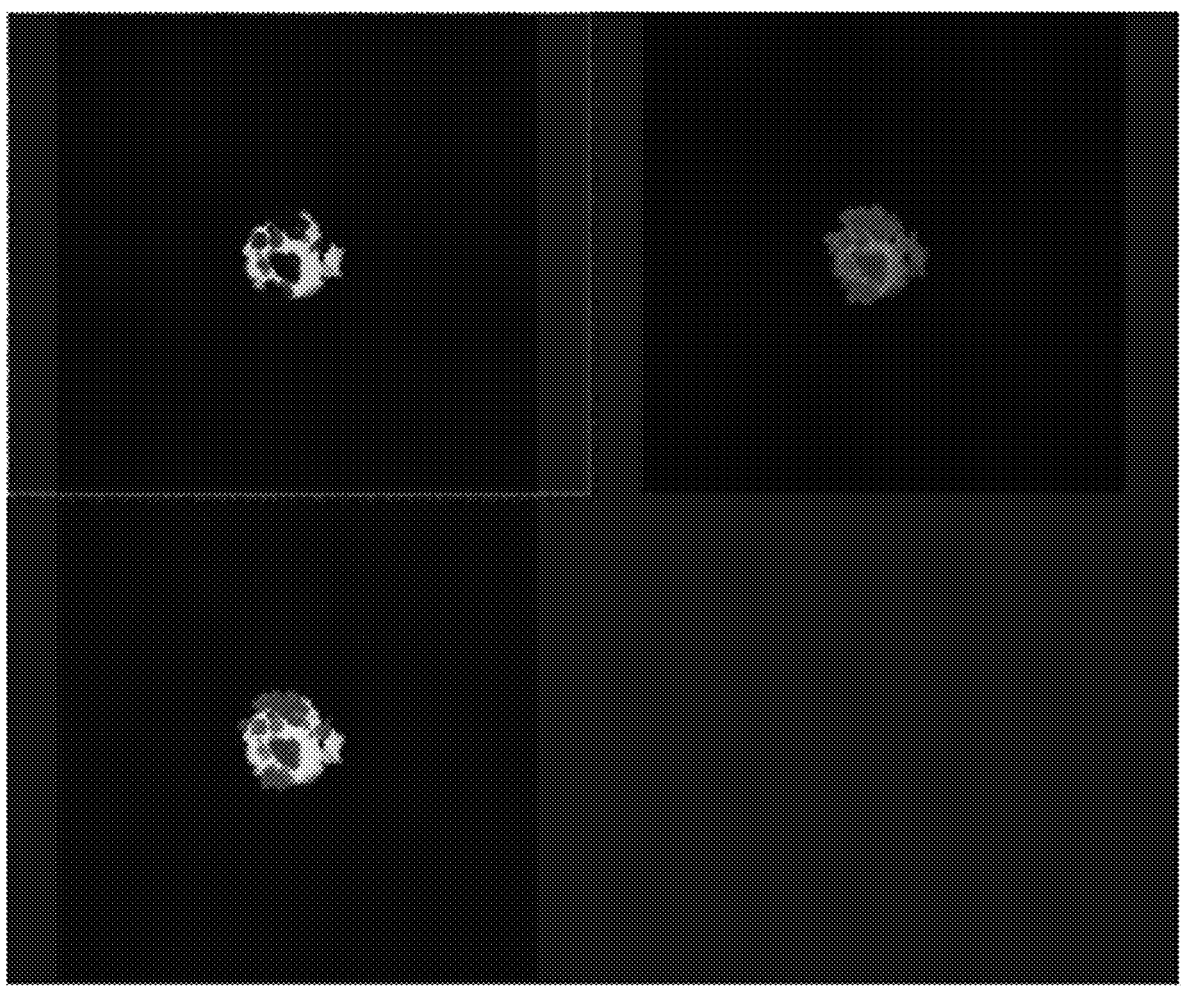
FIG. 9 shows a monocyte cell from the blood of a 25 year old man with severe Crohn's disease stained A4 in red (top right) and XA4P in green (top left). The cell is not perforated so staining is directed to the surface of the cell and almost certainly perturbs its function. The targets of the monoclonal antibodies contain the same amino acid sequence which includes 1 serine residue. This serine is not phosphorylated in the A4 target and is phosphorylated in the XA4P target. The phosphorylation event causes the targets to change their immunogenicity so that although they both crowd the cell surface in close apposition with one another they do not ad-mix. The use of A4 and XA4P monoclonal antibodies therefore allows the actions of the 2 MAP products to be used to trace the molecules and study their locations.

SEQ ID NO: 1 is the amino acid sequence of P900 encoded by the positive strand of MAP IS900 in MAP.

| 1 | MTVTEVVVAQPVWAGVDAGKADHYCMVINDDAQRLLS QRVANDEAALLELIAAVTTLADG |
|---|---|
| 61 | GEVTWAIDLNAGGAALLIALLIAAGQRLLYIPGRTVH HAAGSYRGEGKTDAKDAAIIADQ |
| 121 | ARMRHDLQPLRAGDDIAVELRILTSRRSDLVADRTRA INRMRAQLLEYFPALERAFDYNK |
| 181 | SRAALILLTGYQTPDALRSAGGARVAAFLRKRKARNA DTVAATALQAANAQHSIVPGQQL |
| 241 | AATVVARLAKEVMALDTEIGDTDAMIEERFRRHRHAE IILSMPGFGVILGAEFLAATGGD |
| 301 | MAAFASADRLAGVAGLAPVPRDSGRISGNLKRPRRYD RRLLRACYLSALVSIRTDPSSRT |
| 361 | YYDRKRTEGKRHTQAVLALARRRLNVLWAMLRDHAVY HPATTTAAA |

Underline denotes predicted transmembrane regions

DETAILED DESCRIPTION OF THE INVENTION

The present invention provides a novel method for detecting *Mycobacterium avium* subspecies paratuberculosis using antibodies that specifically bind to the polypeptide encoded by the positive strand of IS900 (P900). The amino acid sequence of MAP P900 is shown in SEQ ID NO: 1.

The present invention relates to a method of detecting the presence or absence of *Mycobacterium avium* subspecies paratuberculosis (MAP) in a sample, which method comprises detecting the presence or absence of the polypeptide (P900) encoded by the positive strand of IS900 (MAP IS900), or a fragment thereof, in a sample from a patient, wherein the MAP P900 polypeptide, or a fragment thereof, is detected using an antibody, or an antigen-binding fragment thereof, that binds to P900.

In particular, the present invention relates to a method of diagnosing or monitoring *Mycobacterium avium* subspecies paratuberculosis (MAP) infection, which method comprises detecting the presence of the polypeptide encoded by the positive strand of IS900 (MAP IS900), or a fragment thereof, in a sample from a patient, wherein the MAP P900 polypeptide, or a fragment thereof, is detected using an antibody, or an antigen-binding fragment thereof, that binds to MAP P900.

Antibody

The present application utilises antibodies, or antibody-binding fragments thereof, that specifically bind to the polypeptide encoded by the positive strand of IS900 (P900) and/or to a fragment thereof. The amino acid sequence of P900 is shown in SEQ ID NO: 1. More preferably, the antibodies, or antibody-binding fragments thereof, bind to a region of P900 extracellular to MAP. The region extracellular to MAP is preferably within amino acids 24 to 71, preferably within amino acids 26 to 71, of SEQ ID NO: 1 (N-terminal extracellular region) or within amino acids 329 to 386, preferably within amino acids 329 to 385, of SEQ ID NO: 1 (C-terminal extracellular region).

The present invention provides antibodies and antibody binding fragments thereof that specifically bind to the N-terminal extracellular region or the C-terminal extracellular region of MAP P900.

Preferred antibodies, or antigen-binding fragments thereof, of the invention include antibodies and antibody fragments which specifically bind to the region of P900 defined by amino acids 26 to 71 of SEQ ID NO: 1 or which specifically bind to a phosphorylated sequence within the region of P900 defined by amino acids 26 to 71 or 329 to 385 of SEQ ID NO: 1.

The antibodies, or antibody-binding fragments thereof, bind to amino acid sequences within P900 that are specific for MAP, i.e. the antibodies, or antibody-binding fragments thereof, bind to a unique MAP sequence. In particular, the sequences to which the antibodies bind are not found in homologous sequences encoded by DNA insertion elements in closely related *M. avium* sp. known in the art, in particular in *M. avium* spp *avium, M. avium* ssp sylvat, *M. avium* 2333, *M. avium* chebnae, *M. porcinum, M. Rhodesiac, M. thermoresistibile, M. avium* 16 p44, *M. avium* 2285; *M. intracellulare; M. xenopi, M avium* p44, *M. avium silvaticum, M. avium hominissuis, Liefsonia xyli* TR and/or *M. avium* AF071067. The antibodies, or antibody-binding fragments thereof, bind to a MAP P900 sequence but do not bind to homologous sequences from other related organisms.

The antibodies, or antibody-binding fragments thereof, may bind to a linear epitope (i.e. to a particular amino acid sequence) within P900. The antibodies, or antibody-binding fragments thereof, are typically generated using a synthetic peptide fragment of P900 as an immunogen. Therefore, the antibodies or antibody fragments, may bind to a peptide fragment of P900. Antibodies that bind to a fragment of P900 as well as to full length P900 may be used in a method of the invention, as may antibodies which bind only to a fragment of P900, particularly where a fragment to which the antibody binds is cleaved from full length P900 in cells infected with MAP which are then progressively depleted of that fragment which may be transferred to another cell. It is preferred that the antibody binds to P900 on the surface of mycobacterial (MAP) cells and host cells infected with MAP. Such antibodies typically also bind to a peptide fragment of MAP.

The antibody, or antigen-binding fragment thereof, may be one that binds specifically to a non-phosphorylated sequence within P900, or one that binds specifically to a phosphorylated sequence within P900. The antibody, or antigen-binding fragment thereof, may be one that binds to an amino acid sequence of P900 regardless of the phosphorylation status of P900.

The P900 polypeptide may be phosphorylated at serine, tyrosine and/or threonine residues. The antibody, or antigen binding fragment thereof, may bind specifically to a P900 sequence that is phosphorylated at one or more of these residues. Preferably the phosphorylated residue is a serine residue. The antibody, or antigen binding fragment thereof, may bind only to a P900 sequence in which one or more serine residue (and/or one or more tyrosine and/or one or more threonine residue) is phosphorylated or only to the P900 sequence in which one or more serine residue including adjacent serine residues (and/or one or more tyrosine and/or one or more threonine residue) is not phosphorylated.

The antibody, or antigen-binding fragment thereof, may bind specifically to a non-phosphorylated sequence within amino acids 24 to 71 or 329 to 386 of SEQ ID NO: 1, such as within amino acids 345 to 371 of SEQ ID NO: 1. The antibody, or antigen-binding fragment thereof, may specifically bind to a phosphorylated sequence within the region of P900 defined by amino acids 24 to 71 or 329 to 386 of SEQ ID NO: 1, preferably within amino acids 26 to 71 or 345 to 371 of SEQ ID NO: 1.

The antibody, or antigen-binding fragment thereof, may specifically bind to an amino acid sequence within:
- residues 24 to 44 of SEQ ID NO: 1 (YCMVINDDAQRLLSQRVANDE (SEQ ID NO: 14)—designated the A0X site), preferably residues 26 to 39 of SEQ ID NO: 1 (MVINDDAQRLLSQR (SEQ ID NO:2)—designated A0X) or residues 26 to 39 in which S37 is phosphorylated (MVINDDAQRLL[pS]QR (SEQ ID NO: 3)—designated AOXP);
- residues 52 to 71 of SEQ ID NO: 1 (AAVTTLADGGEVTWAIDLNA (SEQ ID NO:15)—designated the XA1 site), preferably residues 52 to 68 of SEQ ID NO: 1 (AAVTTLADGGEVTWAID (SEQ ID NO: 10)—designated XA1); or
- residues 329-360 of SEQ ID NO: 1 (NLKRPRRYDRRLLRACYLSALVSIRTDPSSRT (SEQ ID NO: 16)), preferably residues 329 to 343 of SEQ ID NO: 1 (NLKRPRRYDRRLLRA (SEQ ID NO:11)—designated A3), residues 345 to 359 of SEQ ID NO: 1 (YLSALVSIRTDPSSR (SEQ ID NO:4)—designated XA4), residues 345 to 359 of SEQ ID NO: 1 in which one or more of the serine residues is phosphorylated, preferably in which either S357 (YLSALVSIRTDP[pS]SR (SEQ ID NO:7)) or S358 (YLSALVSIRTDPS[pS]R (SEQ ID NO:6)—designated XA4P) is phosphorylated or both S357 and S358 are phosphorylated (YLSALVSIRTDP[pS][pS]R (SEQ ID NO:13));
- residues 350 to 359 of SEQ ID NO: 1 (VSIRTDPSSR (SEQ ID NO:5)—A4), or residues 350 to 359 of SEQ ID NO: 1 in which either S357 or S358 is phosphorylated or both S357 and S358 are phosphorylated;
- residues 370-386 of SEQ ID NO: 1 (KRHTQAVLALARRRLNV (SEQ ID NO:17)); or
- residues 370-385 of SEQ ID NO: 1 (KRHTQAVLALARRRLN (SEQ ID NO: 18)).

The antibody may be a monoclonal or polyclonal antibody, preferably a monoclonal antibody, or antigen-binding fragment thereof. The antibody may be a human, humanised or chimeric antibody, or may be a mouse antibody or antibody from another species such as Rabbit, Goat, Donkey or Alpaca. The antibody may be a recombinant antibody.

The term "antigen-binding fragment" of an antibody refers to one or more fragments of an antibody that retain the ability to specifically bind to MAP P900 and/or a peptide fragment of MAP P900. Examples of suitable fragments include a Fab fragment, a F(ab')2 fragment, a Fab' fragment, a Fd fragment, a Fv fragment, a dAb fragment and an isolated complementarity determining region (CDR). Single chain antibodies such as scFv and heavy chain antibodies such as VHH and camel antibodies are also intended to be encompassed within the term "antigen-binding portion" of an antibody. The antigen-binding fragment may, for example, be: a single domain 'Nanobody' (Fridy et al. "A robust pipeline for rapid production of versatile nanobody repertoires." Nature Methods. 2014; 11: 1253-1260); a pegylated fragment; a bispecific fragment (e.g. two scFv fragments joined by a peptide linker); conjugated to a bacterial toxin, or a mutated form thereof, such as *Pseudomonas* exotoxin A or Staphylococcal enterotoxin A; conjugated to polyethylene glycol; a tandem diabody; or a dual affinity re-targeting (DART) molecule (Sheridan "Ablynx's nanobody fragments go places antibodies cannot" Nature Biotechnology 2017 35: 1115-1117).

The antibody, or antigen-binding fragment thereof, may be labelled. The label aids in the detection of the antibody bound to P900 in the detection methods of the invention. The label may be a fluorophore, an enzyme such as Horse Radish Peroxidase, gold beads, a radioisotope, or a tag such as a particular synthetic peptide epitope or a synthetic oligonucleotide or a lanthanide. Any suitable fluorophore may be used to label the antibody, or antigen-binding fragment. For example, the fluorophore may be green fluorescent protein, rhodamine, Oregon green, eosin or Texas red. Where the method of the invention uses a pair of antibodies, or antigen-binding fragments thereof, each member of the pair is preferably labelled differentially, for example with differently coloured fluorophores, such as a red fluorophore and a green fluorophore, so that binding of each of the antibodies to the sample may be distinguished and/or so that co-localisation of the antibodies may be detected.

Diagnosing and Monitoring MAP Infection

The invention provides the use of an antibody, or antigen-binding fragment thereof, according to the invention in an ex vivo method of diagnosing or monitoring MAP infection. The method may further comprise treating a subject diagnosed as having a MAP infection. The method may further comprises altering the treatment of a subject having a MAP infection, wherein the MAP infection is being monitored in the subject. For example, the treatment may be a treatment in which one or more antimicrobial agent, such as a combination including Rifabutin and Clarithromycin, is administered to the patient, either alone or in combination with one or more additional therapeutic agents. The treatment may be a prophylactic or therapeutic MAP vaccine. The treatment may comprise passive immunotherapy administering to the subject anti-MAP monoclonal antibodies such as the antibodies described herein.

The method of detecting MAP P900 provided by the invention may be used to detect MAP infection in a subject. Typically the method is carried out ex vivo using a sample taken from a human or animal subject. The subject may have, or be suspected of having, Crohn's disease, psoriasis, thyroiditis, Parkinson's disease, Multiple Sclerosis, type 1 diabetes, arthritis, ankylosing spondylitis, colitis, inflammatory bowel disease or irritable bowel syndrome, Alzheimer's disease, sarcoidosis, idiopathic pulmonary fibrosis and/or chronic fatigue syndrome. The subject may be a healthy subject. A healthy subject is a human or animal having no symptoms of a disease associated with MAP infection, such as any of the diseases listed above. In animals the subject may be suspected of being infected with MAP or of having Johne's disease. The animal may be any animal, but is preferably a laboratory animal, a wild animal, a pet or is more preferably a farm animal. The farm animal is preferably an animal used for milk production or for meat, such as a cow, goat, sheep or deer. The method may be used to diagnose MAP infection or to monitor MAP infection. MAP infection may be monitored to determine the progress of the infection. Accordingly, the method of the invention may be used to study the course of MAP infection and/or to determine the status of the infection in a subject.

The antibodies, or antibody binding fragments thereof, specific for MAP P900 may be used singly, or in multiples, to diagnose, quantify and characterise MAP infections in humans and animals. For example, one, two, three, four, five or more antibodies may be used in a method of the invention. Typically the antibodies used in a method of the invention will be specific for different P900 sequences and/or for the same P900 sequences but in phosphorylated and non-phosphorylated forms.

The present inventor has found that infection with MAP, and/or cells in a subject infected with MAP, can be detected using antibodies specific for MAP P900 to stain tissue samples taken from a subject. The staining can be viewed by any suitable means. Microscopy, in particular confocal microscopy, can be used to identify cells of a subject infected with MAP. MAP can be seen as distinct subcellular particles within infected cells. The antibodies specific for MAP P900 may also be used to detect MAP P900 on the surface of the infected cells of a subject.

Furthermore, the method of the invention may comprise determining whether the region of MAP P900 between amino acids 26 to 71 and/or 273 to 406 of SEQ ID NO: 1, or a fragment of either thereof, has been cleaved from membrane-bound MAP P900.

One way to do this is to use at least one antibody that specifically binds to a first region of P900, such as the region between amino acids 26 to 71 of SEQ ID NO: 1, and at least one antibody to a second region of P900, such as the region between amino acids 273 to 406 of SEQ ID NO: 1. A fragment of P900 has been cleaved and released where the antibody to the first region of P900 does not co-localise with the antibody to the second region of P900. In this situation, there may be some partial co-localisation of the two antibodies, depending on the degree of cleavage and release. Co-localisation of antibodies may be determined by any suitable method. For example, a first antibody may be labelled with a green fluorophore and a second antibody with a red fluorophore. Binding of the labelled antibodies to the sample may be visualised using a suitable microscope (such as a confocal microscope). Observation of green or red staining indicates areas where just one of the first and second antibodies is bound, whereas gold, orange or yellow staining shows where both antibodies are co-localised.

The fragment cleaved from P900 may be within the region 329 to 386, 329 to 385, or 370 to 386 of SEQ ID NO: 1. Typically the fragment may be detected using an antibody, or antigen-binding fragment thereof that binds to amino acids 329-360 of SEQ ID NO: 1, preferably residues 329 to 359, 329 to 343, 345 to 360, 345 to 359, 350 to 359 or 350 to 360 of SEQ ID NO: 1, residues 329 to 360, 329 to 359, 345 to 360 or 345 to 359, 350 to 359 or 350 to 360 of SEQ ID NO: 1 in which either S357 or S358 is phosphorylated or both S357 and S358 are phosphorylated.

The cleaved fragment detected by a method of the invention may be detected in cells of the subject that are not infected with MAP cells, but that are adjacent to or close to infected host cells. In such cells, the antibodies stain the cytoplasmic compartment. The presence of a MAP P900 fragment in the cytoplasmic compartment of cells of the subject may be used as an indicator of the stage of MAP infection.

The sample tested in a method of the invention may a sample of a tissue. The tissue is typically taken from the site of suspected infection. The tissue sample may be a sample of skin, a sample from the mouth, gastrointestinal tract, thyroid, lung, lymph node, brain or genitourinary tract. The sample may be a gut biopsy, particularly where the subject has Crohn's disease or is suspected of having Crohn's disease or another gastrointestinal disorder such as colitis, inflammatory bowel disease or irritable bowel syndrome. The gut sample may be taken from any one or more of the oesophagus, stomach, duodenum, jejunum, ileum, cecum, appendix, colon and rectum and the perianal region. The method of the invention may also be used to monitor vasculitis, by monitoring MAP infection in the blood vessels, for example in the blood vessels of the gut. The sample may be skin where the subject has or is suspected of having Psoriasis. The sample is typically a thyroid sample where the subject has or is suspected of having Hashimoto's thyroiditis.

MAP P900 and/or fragments thereof may also be detected in the blood and in other bodily fluids, such as breast milk or synovial fluid, from a subject infected with MAP. The sample tested in a method of the invention may therefore be a sample of a bodily fluid such as blood, urine, semen, amniotic fluid, cerebrospinal fluid, synovial fluid, and sputum or breast milk.

The status of the MAP infection may also be determined using antibodies specific for non-phosphorylated P900 and antibodies that are specific for phosphorylated P900. Typically the method uses antibodies that bind to the same amino acid sequence of P900, wherein a first antibody binds to the non-phosphorylated sequence and the second antibody binds to the phosphorylated sequence.

For example, antibodies that bind to MVINDDAQRLLSQR (SEQ ID NO:2) can be used to detect the presence of P900 in gut tissues, whereas antibodies that bind to MVINDDAQRLL[pS]QR (SEQ ID NO: 3) do not stain gut tissues in humans. However, antibodies to MVINDDAQRLL[pS]QR (SEQ ID NO: 3) do bind to P900 or a fragment thereof in infected white cells in human blood (WBC) so that the presence of MVINDDAQRLL[pS]QR (SEQ ID NO: 3) in blood may indicate the progression of the MAP infection from gut to blood in the subject.

Antibodies to phosphorylated and non-phosphorylated forms of the same or similar P900 sequence, preferably MVINDDAQRLLSQR (SEQ ID NO:2) (A0X) and MVINDDAQRLL[pS]QR (SEQ ID NO: 3) (A0XP) or VSIRTDPSSR (SEQ ID NO:5) (A4) and YLSALVSIRTDPS[pS]R (SEQ ID NO:6) (XA4P), may be used to provide a measure of the level of MAP infection. In this situation the non-phosphorylated form of the sequence is the substrate and the phosphorylated sequence is the product of the activity of the phosphorylating enzyme. The substrate and the product are in a dynamic relationship with each other where depletion of substrate is matched by increase in product. At a given point in time, the sum total of circulating white blood cells (WBCs) and their individual lineages containing either the substrate, the product or both the substrate and the product provides a measure of the proportion of circulating WBCs infected with MAP. The ratio between the non-phosphorylated and phosphorylated peptides reflects the activity of the system likely to provide clinical correlates of disease activity and responses to treatments. Typically where the antibodies are mutually exclusive, e.g. bind to either the phosphorylated sequence or to the non-phosphorylated sequence but not to both, the total amount of antibody binding gives an indication of the total amount of P900 present in the sample and the proportion of host cells infected with MAP. For example, the number and/or proportion of infected WBCs may be determined using the A0X and A0XP antibodies to detect MAP in WBCs. The number and/or proportion of infected WBCs correlates with the severity of infection. The severity of infection also correlates with inflammatory symptoms in the infected individuals, for example in people with Crohn's disease. In individuals with Crohn's disease, the percentage of infected WBCs in the blood has been shown to be as high as about 50%, but may be lower as shown in Table 2.

The present inventor has demonstrated that the C-terminus of MAP P900 is cleaved by showing that A0X and/or A0XP antibody staining of the N-terminus does not always co-localise with XA4 and/or XA4P staining of the C-terminus. The antibodies and antibodies of the present invention may therefore be used to monitor the pathogenic mechanism involving the cleavage, release and/or trafficking of the C-terminus of MAP P900. The method of the invention may be used to monitor MAP infection following treatment of a subject. The treatment of the subject may be a treatment intended to target the MAP infection, or a treatment of a disease that is associated with or caused by MAP infection, such as Crohn's disease, Psoriasis, Thyroiditis, Parkinson's disease, Multiple Sclerosis, Alzheimer's disease, type 1 Diabetes, Arthritis, Ankylosing Spondylitis, Colitis, Inflammatory Bowel Disease or Irritable Bowel Syndrome, Sarcoidosis, idiopathic pulmonary fibrosis and/or chronic fatigue syndrome. Thus, the invention provides a method for monitoring the effectiveness of a treatment of MAP infection, or the effect of a treatment for any of the above conditions, or other condition, on MAP infection. For example, the treatment may be a treatment in which one or more antimicrobial agent, such as a combination including Rifabutin and Clarithromycin, is administered to the patient, either alone or in combination with one or more additional therapeutic agents. The treatment may be a prophylactic or therapeutic MAP vaccine. The treatment may comprise passive immunotherapy administering to the subject anti-MAP monoclonal antibodies such as the antibodies and peptides described herein.

Uses of the Invention

The method of the invention may be used to detect MAP contamination of clinical, environmental and/or food samples. In such methods, the antibodies, or antibody binding fragments thereof, specific for MAP P900 may be used singly, or in multiples. For example, one, two, three, four, five or more antibodies may be used in a method of the invention. Typically the antibodies used in a method of the invention will be specific for different P900 sequences or for the same P900 sequences but in phosphorylated and non-phosphorylated forms.

The invention also provides the use of an antibody, or antigen-binding fragment thereof, of the invention to detect MAP in a human or animal food sample or environmental sample.

The food sample may be a sample of a food product such as milk or other dairy product or a meat product. MAP infection is known to be widely present in domestic livestock including dairy and beef cattle, sheep and goat flocks as well as farmed deer. The infection is known to be systemic and as the present technology has confirmed, these pathogens can be abundantly present in blood even in the absence of clinical signs or the presence of positive conventional diagnostic tests such as ELISA. A particular feature of MAP infection is the passage of MAP laden cells into milk of all species tested, so that offspring are exposed to the more virulent intracellular form of MAP soon after birth, when they are most susceptible. MAP is more thermostable than *M. tuberculosis* and can survive pasteurisation conditions. Human populations are exposed to MAP in retail pasteurised milk supplies. The best test presently available for MAP in milk is PCR based which is too technically demanding and costly for widespread application.

The environmental sample is typically a sample of surface water, river water, domestic water, and water treatment plant water, an aerosol, soil or sediment. The technical difficulties which have affected MAP testing of clinical samples also apply to those used in testing MAP in samples from its catchment, between release from an infected animal into the environment, to human exposure. The antibodies, antibody fragments and peptides of the invention may be used to capture and measure MAP.

Peptides

The invention provides immunogenic MAP peptides. The peptide may comprise amino acids 26 to 71 of SEQ ID NO: 1, or a fragment of this sequence. The fragment typically comprises at least 10 amino acids, such as at least 11, 12, 13, 14 or 15 amino acids. The fragment may have an upper limit of 20, 25, 30, 35, 40 or 44 amino acids. The fragment may be a fragment of residues 24 to 44 of SEQ ID NO: 1, or may be a longer fragment comprising residues 24 to 44 of SEQ ID NO: 1. Preferred fragments include a fragment consisting of or comprising residues 26 to 39 of SEQ ID NO: 1 and a fragment consisting of or comprising residues 52 to 68 of SEQ ID NO: 1, such as a fragment comprising or consisting of residues 52 to 71 of SEQ ID NO: 1.

The peptide may comprise or consist of amino acids 345 to 359 of SEQ ID NO: 1. The peptide comprising amino acids 345 to 359 of SEQ ID NO: 1 may have length of from 16 to 40 amino acids, such as from 20 to 30 or 22 to 27 amino acids, for example 25 amino acids and is typically a fragment of P900.

The invention provides a phosphorylated peptide which comprises amino acids 26 to 71 of SEQ ID NO: 1 or amino acids 329 to 385 of SEQ ID NO: 1, or a fragment of either of these sequences, such as amino acids 345 to 371 of SEQ ID NO: 1, in which one or more serine residue and/or one or more tyrosine residue and/or one or more threonine residue is phosphorylated. Examples of phosphorylated peptides of the invention comprise or consist of amino acids 26 to 39 of SEQ ID NO: 1 in which S37 is phosphorylated, residues 350 to 359 of SEQ ID NO: 1 in which either S357 or S358 is phosphorylated or both S357 and S358 are phosphorylated. A peptide comprising one of these phosphorylated sequences may have length of from 15 to 40 amino acids, such as from 20 to 30 or 22 to 27 amino acids, for example 25 amino acids, and is typically a fragment of P900. The peptide may be phosphorylated at one or further serine residue and/or at one or more tyrosine residue and/or at one or more threonine residue. Such longer fragments include a peptide consisting of or comprising residues 345 to 359 of SEQ ID NO: 1, such as a peptide consisting of or comprising residues 329-360 of SEQ ID NO: 1.

The peptide of the invention may be modified at the N-terminus and/or at the C-terminus and/or may be conjugated or coupled to a carrier molecule. Peptides may, for example, be conjugated to a bacterial saccharide or a carrier protein, such as keyhole limpet hemocyanin (KLH), bovine serum albumin (BSA), human serum albumin (HSA) or ovalbumin (OVA). The peptides may be biotinylated at the N-terminal or C-terminal, may be amidated at the N-terminal or C-terminal and/or may have a peptide tag added at the N-terminal or the C-terminal. The peptide tag may be, for example, a polylysine, such as a branched polylysine octamer, or a cell penetrating peptide such as an oligoarginine (e.g. a polyarginine octamer or nonomer). Preferably, the peptide is biotylated at the N-terminus and has an amide group or a branched polylysine octamer at the C-terminus. One or more additional amino acid residues may be added at the N-terminus and/or the C-terminus, optionally in addition to other terminal modifications. For example, one or more, such as two, alanine residues may be added at the N-terminus to increase immunogenicity and specificity and/or charged residues, for example GKK may be added at the N-terminus or preferably the C-terminus to reduce hydrophobicity. Where residues, such as GKK, are added at one terminus, the mirror image residues, such as KKG, may be added at the other terminus.

The present invention also provides polynucleotides encoding the peptides and antibodies of the invention, as well as expression vectors comprising such polynucleotides and host cells comprising such expression vectors.

Uses of Peptides

The peptides of the invention may be used to generate antibodies for use in the present invention. The invention provides a peptide according to the invention for use as an immunogen.

The invention provides a method of generating an antibody that specifically binds to MAP P900, which method comprises administering a peptide of the invention to a laboratory animal to generate an immune response and isolating antibodies from the animal. The animal may, for example, be a mouse, rabbit, rat, goat, donkey, alpaca. The method may further comprise screening the isolated antibodies. The isolated antibodies may be screened for specific binding to MAP P900 by determining whether the antibodies bind to a peptide of the invention and whether the antibodies bind to homologous peptides from one or more related organisms. A peptide is selected as being specific for MAP P900 where it binds to a peptide of the invention but does not bind to the homologous peptides from related organisms, or binds to the related peptide(s) to lesser extent than to the MAP peptide, for example showing 30% or less, 20% or less, 10% or less, 5% or less binding. For example, at least one, such as 2, 3, 4, 5, 6, 7, 8, 9, 10 or more related organisms may be chosen. The related organisms are typically other *M. avium* sp and may, for example, be selected from *M. avium* spp *avium*, *M. avium* ssp *sylvat*, *M. avium* 2333, *M. avium* chebnae, *M. porcinum*, *M Rhodesiac*, *M thermoresistibile*, *M. avium* 16 p44, *M. avium* 2285; *M. intracellulare*; *M. xenopi*, *M. avium* p44, *M. avium* silvaticum, *M. avium* hominissuis, *Liefsonia xyli* TR and *M. avium* AF071067. Exemplary peptides from related organisms are described in the Examples.

Hybridomas producing monoclonal antibodies of the invention may be generated by standard methods.

Antibodies may be screened/validated in any of the following ways:
1. Staining of cultured MAP and related mycobacteria in their extracellular phenotype.
2. Staining of cultured MAP and related mycobacteria in their intracellular phenotype in cell culture.
3. Western blots of MAP and other mycobacterial lysates and developing the blots.
4. ELISA of monoclonal antibody binding to the same peptides in MAP and related peptides in other organisms.

Laser capture microdissection of stained and unstained areas in tissues followed by DNA extraction, MAP specific PCR and verification by amplicon sequencing.
6. Fluorescence activated cell separation of antibody stained cells and PCR.
7. Differential blockade of antibody staining of tissues by the identical synthetic target peptide and not by unrelated peptides.

Exemplary methods are described in the Examples.
8. Colocalisation of multiple monoclonal antibodies on submicrometre MAP particles in the cytoplasm of infected cells.

Medical Uses/Methods of Treatment

The invention provides an antibody or antigen-binding antibody fragment according to the invention for use in therapeutic or diagnostic method carried out on the human or animal body. The therapeutic method is typically treatment or prevention of MAP infection in a subject. The diagnostic method is typically diagnosis of MAP infection.

The invention also provides the use of an antibody or antigen-binding antibody fragment according to the invention in the manufacture of a medicament for use in a method of treating, preventing or diagnosing MAP infection.

Also provided by the invention is a method of treating or preventing MAP infection in a subject in need thereof, which method comprises administering to the subject a therapeutically or prophylactically effective amount of an antibody or antigen-binding antibody fragment according to the invention. The subject may have none, one or more of the following diseases: Crohn's disease, psoriasis, thyroiditis, Parkinson's disease, type 1 diabetes, arthritis, ankylosing spondylitis, irritable bowel syndrome, ulcerative colitis, inflammatory bowel disease, Alzheimer's disease, multiple sclerosis, sarcoidosis, idiopathic pulmonary fibrosis and/or chronic fatigue syndrome.

The following Examples illustrate the invention.

Example 1: Phases of Development of the Antibodies of the Invention

Phase 1. Mapping Mouse Antibody Binding Peptide Domains in P900

99.6% of the MAP genome is virtually identical in DNA sequence and genetic organisation to those of other *M. avium* sp which are ubiquitous in the environment and in healthy animals and humans. Therefore, finding unique targets on MAP which are sterically accessible and abundantly expressed during intracellular infection in humans is difficult. Of the 4,377 ORFs predicted in the MAP genome, the gene encoding IS900 (NCBI accession: AE016958.1) was selected. IS900 is a DNA insertion element of 1451-53 bp discovered by the present inventor and colleagues late in 1985 in three Crohn's disease isolates of MAP (E. Green et al Nucleic Acids Research 1989; 17: 9063-73). It is present in MAP in 14-18 identical copies inserted at highly conserved sites throughout the MAP genome. This multicopy element has its own promoter, is abundantly expressed in humans and contributes to the broad pathogenic phenotype.

The positive strand of IS900 predicts a protein (P900) of 406 amino acids. Its full length amino acid sequence is unique to MAP but there are P900 'look-alikes' in closely related mycobacteria and actinomycetes which cover most of the P900 molecule.

Full length P900 protein encoded by the positive strand of IS900 is toxic for *E. coli* cells. A less toxic truncated version consisting of amino acids 49 to 377 of P900 was made and expressed as the recombinant protein in *E. coli*.

Ten mice were immunised with the recombinant truncated P900 protein adherent to magnetic beads because the free recombinant protein was found not induce a satisfactory immune response. The sera from immunised mice were screened by ELISA against immobilised P900 and 4 positive mice were identified. Spleen cells from these mice were used for hybridoma fusion resulting in 10 parental clones. Supernatants from these and their successive subclones were screened against a library of 64 synthetic 15 amino acid peptides overlapping by 10 amino acids spanning the truncated P900 amino acid sequence from ELIAAVTTLADG-GEV (SEQ ID NO:19) . . . to . . . DRKRTEGKRHTQAVL (SEQ ID NO:20). The antibodies were all IgM and the clones eventually proved unstable. Despite the inability to obtain the desired monoclonal reagents, 8 peptides or peptide clusters were identified as immunogenic within the truncated P900 protein. In the peptide library these involved peptides No. 2-VTTLADGGEVTWAID (SEQ ID NO:12), 27-NKSRAALILLTGYQT (SEQ ID NO:21), 41-AKEVMALDTEIGDTD (SEQ ID NO:22), 42-ALDTEIGDTDAMIEE (SEQ ID NO:23) and a cluster within the sequence GRISGNLKRPRRYDRRLLRACYLSALVSIRTDPSSRTYYD (SEQ ID NO:24).

Bio-informatics was used to examine these candidate sequences taking into account: (i) specificity for MAP especially compared with homologous sequences encoded by DNA insertion elements in closely related *M. avium* sp well known in the art; (ii) predicted location on the external surface of MAP accessible to antibodies; and (iii) predicted sites for post translational modifications such as phosphorylation, myristilation, glycosylation, signalling motifs and limited proteolytic cleavage sites which might affect antibody recognition, location within a MAP-infected cell, trafficking, stability, transport and function.

TABLE 1

Examples of peptides similar to A1 A3 and A4 in other organisms

| Peptide | Sequence | Organism |
|---|---|---|
| A1 reference | VTTLADGGEVTWAIDLNA (SEQ ID NO: 37) | MAP K-10 bovine, all MAP strains including Sheep S397 |
| | VTRLADGGEVTWAVD (SEQ ID NO: 25) | M avium 16 p44 |
| | VATMADGGEVTWAID (SEQ ID NO: 26) | M porcinum ABV59207; M Rhodesiae WP014211331.1; M thermoresistible WP040548537 |
| | VTRLADGGEVTWAVD (SEQ ID NO: 25) | M avium 2285 EUA29312.1; M intracellulare EUA53942.1; M avium subsp. avium P44 CAA09798.1 |
| | VTAQADGGDVTWAID (SEQ ID NO: 28) | M xenopi 4042 EUA52288.1 |
| A3 | NLKRPRRYDRRLLRAGYL (SEQ ID NO: 39) | MAP and M avium EMBLAAF08611.1 Japan IS1626 |
| | NLQRPRRYNRRLLRA (SEQ ID NO: 29) | M porcinum |
| | NLKRPRRYDRRLLRT (SEQ ID NO: 30) | M avium p44 |
| | NLHRPKRYNRRLRRV (SEQ ID NO: 31) | M avium silvaticum |
| | NLHRPKRYNRRLRRV (SEQ ID NO: 31) | M avium hominissuis |
| | NLHRPKRYDRRLLRA (SEQ ID NO: 33) | Liefsonia xyli TR: Q6ACG7 AE016822 |

TABLE 1-continued

Examples of peptides similar to A1 A3 and A4 in other organisms

| Peptide | Sequence | Organism |
|---|---|---|
| A4 | YLSALVSIRTDPSSR (SEQ ID NO: 4) | MAP |
| | YLSALYSIRSDPASR (SEQ ID NO: 34) | M porcinum, M thermoresistible |
| | YTSALVSVRYDPSSR (SEQ ID NO: 35) | IS116/110/902 |
| | YLSAQIAIRTDPASR (SEQ ID NO: 36) | M avium AF071067 and P44 |

Phase 2. Preparation of Polyclonal Antibodies to P900 Sequences in Rabbits and their Testing on Humans and Animals.

Polyclonal antibody preparation: Preferred initial peptides designated A1-VTTLADGGEVTWAIDLNA (SEQ ID NO:37), A2-NKSRAALILLTGYQTPDA (SEQ ID NO: 38), A3-NLKRPRRYDRRLLRAGYL (SEQ ID NO: 39), and A4-YLSALVSIRTDPSSR (SEQ ID NO:4) were identified. These were prepared as synthetic branched octapeptide immunogens on polylysine cores and used to immunise rabbits. Suitable titres of polyclonal antibodies were readily achieved for A1, A3, and A4. A2 was not immunogenic the rabbit. A2 was also intracellular in MAP and was not studied further.

Antibodies in A1 and A3 sera reacting with Freund's complete adjuvant (M tuberculosis H37Ra, Difco, USA) were abstracted to completion using excess antigen. Only Freund's incomplete antigen was used as the adjuvant with A4. Rabbit polyclonal reagents A1, A3 and A4 were applied in preliminary studies to explore their ability to detect their target sequences and therefore MAP immunoreactivity in human and animal tissues and human blood.

MAP immunoreactivity in human tissues: In an initial study, fresh intestinal mucosal biopsies were obtained from 14 patients diagnosed with Crohn's disease (CD) attending the endoscopy clinic at St Thomas' Hospital, London, UK and 10 control patients without inflammatory bowel disease (nIBD) attending for screening or follow up. Ethical approval was given by the Local Ethics Committee (EC03/053). Biopsies were embedded in Jung tissue freezing medium and snap frozen in liquid nitrogen in the endoscopy suite. They were then taken to the laboratory where they were coded and stored −80° C. prior to use.

Orientated biopsies were subsequently cut in 6 μm sections and mounted on PTFE coated slides and stained with A1, A3 and A4 polyclonal antibodies at a dilution of 1:400 to 1:800. Host cell phenotypic markers were CD3 for T cells, CD8 for monocytes/macrophages, CD19 for B cells, CD66b for neutrophils, CD83 for Dendritic cells, PgP9.5 for Glial cells and CD31 for endothelium. Secondary antibodies were rabbit anti-mouse TRITC (R0270 Dako, UK), rabbit anti-mouse FITC (F0261, Dako), swine anti-rabblt TRITC (R0156, Dako), swine anti-rabbit FITC (F0205, Dako) and goat anti-mouse FITC (F0479). Slides were washed ×3 in PBS and mounted in Fluoromount agent (F4680 Sigma-Aldrich, UK) followed by a coverslip.

Use of antibodies A1, A3 and A4 alone at concentrations of 1:500 to 1:800 resulted in staining of cells within the epithelium and in the underlying lamina propria. Antibodies were then used in pairs with A1 labelled with TRITC (red) and A3 or A4 with FITC (green).

The A1 site is located on the extracellular aminoterminal domain of the P900 protein adjacent to the first transmembrane region and right up against the surface of the microbial cell. The A1 peptide appeared to remain attached to MAP.

The A3 and A4 sites are located at the centre of the longer carboxyterminal extracellular domain either side of Cysteine 344. The carboxyterminal domain may either be attached or released by limited proteolytic cleavage close to the second transmembrane region.

Use of A1 (red) and A4 (green) with the carboxyterminal peptide still attached resulted in colocalisation (gold) not only in the same cells but also on submicrometre particles within the cytoplasm of infected cells. Release of the carboxyterminus resulted in a progressive gradient of colour change from gold to orange to red and the visible migration of the released peptide (green) in the cytoplasm of the affected cell. Other cells were seen to contain green only suggesting the ability of released carboxyterminal peptide to traffic to other cells which did not themselves contain MAP. This was supported by the appearance in tissues of intercellular vesicles filled green consistent with endosomes.

In the surface epithelium MAP was seen to infect enterocytes as well as intra-epithelial cells consistent with lymphocytes and macrophages. MAP was seen to cluster often in a 'necklace' around the base of the mucus vacuole of goblet cells releasing green carboxyterminal peptides which migrated in the cytoplasm to the apex of these cells as well as within the mucus vacuole itself.

MAP was also seen to infect cells widely in the lamina propria and particularly clusters of cells around the bases of crypts. Staining involved particularly macrophages, polymorphs and B-lymphocytes but not T-lymphocytes although the presence of T-lymphocytes adjacent to MAP clusters was frequently noted.

Abundant MAP infection in endoscopic mucosal biopsies was seen in all 14 patients with Crohn's disease. Scant clusters of immunoreactive MAP were seen in 8 out of the 10 control subjects. The other 2 control subjects contained no MAP staining at all. The addition of specific peptide to the operational buffer completely blocked staining of tissues by the corresponding antibody. Use of other peptides had no effect on antibody binding. Together with colocalisation this specific blockade reinforced the precision and specificity of the MAP detection system.

PCR Verification of A1 Antibody Binding to MAP in Human Tissues:

Lasermicrodissection pressure catapulting (LMPC) of A1 immunoreactive loci was carried out to determine whether antibody recognition in tissues equated with the presence of MAP using IS900 PCR. Fresh endoscopic mucosal biopsies were obtained from 11 consenting patients and 4 control subjects without inflammatory bowel disease. Tissues were snap frozen in liquid nitrogen and 6 μm cryostat sections were cut as previously described. Sections were transferred to PTFE-coated microscope slides for routine H&E staining. Those for LMPC were immobilised on PEN-membrane slides (Carl Zeiss MicroImaging GmbH, Germany).

Immunoreactive MAP regions were identified in sections with A1 rabbit polyclonal antibody using biotinylated alkaline phosphatase H tagged 2n d antibody to rabbit immunoglobulin. After washing slides in PBS, Vectastain Universal ABC-AP kit (Vector Laboratories UK) was used for localisation of immunoreactive MAP regions according to the manufacturer's instructions. Secondary antibodies were localised using the Vector Blue Alkaline Phosphatase Substrate Kit 1 (Vector Laboratories UK).

Lasermicrodissection and pressure catapulting was used to isolate immunoreactive (IR) and non-immunoreactive (nIR) MAP regions using the Zeiss PALM MicroBeam Laser microdissection system. Prior to microdissection, particular care was taken to ensure that sections were completely air dried so that excised regions readily detached. IR and nIR regions were identified visually and the adhesive cap tube positioned above the selected area. Samples were accumulated onto the cap of the adhesive tube. DNA extraction was carried out as described (T. Bull et al. 2003 J Clin Microbiol 2003; 41:2915-23). Briefly, 2004, of *Mycobacterium* Lysis Buffer (MLB), 8.6 ml molecular-grade water, 8004, 5M NaCl, 1M 10× Tris-EDTA (TE) and 600 µL 10% SDS was added to each tube and incubated overnight at 37 deg C. 10 µL of 10 mg/ml Proteinase K (Sigma), 54, of 100 mg/ml Lysozyme (Sigma) and 4 µL of 120 mg/ml Lipase (Sigma) in MLB were added to each tube and incubated at 37° C. for a further 3 hours. Samples were transferred to Lysing Matrix B ribolyser tubes and 400 µL 1×TE added. Tubes were mechanically disrupted at 6.5 $ms^2$ for 45 seconds on a FastPrep Ribolyser instrument. Standard phenol-chloroform-isoamyl DNA extraction procedure was carried out. Purified DNA was resuspended in 50 µL 1×TE. Nested PCR using 2 µL of template DNA was carried out using L1 and L2 first round primers and AV1 and AV2 second round primers. The expected 298 bp PCR amplicon was visualised using 1% agarose gel electrophoresis. Stringent precautions were taken as described to exclude amplicon contamination.

All 4 control subjects tested negative by IS900 PCR. Immunoreactive regions from 7 of the 11 patients in the CD group were positive for MAP by IS900 PCR, confirmed by amplicon sequencing in 5. All the nIR regions sampled in CD patients were PCR negative. All 7 patients testing positive for MAP by IS900 PCR were undergoing treatment with azathioprine alone. The 4 PCR negative samples came from Crohn's disease patients receiving treatment with azathioprine in combination with Humira or 6-mercaptopurine and Infliximab.

MAP detection in formalin-fixed paraffin-embedded histopathology blocks: The ability of the diagnostic system for MAP in tissues to operate on routine fixed paraffin embedded histopathology samples substantially facilitates its clinical and commercial application. Furthermore it allows the test to be applied retrospectively to archive materials so that, with appropriate approvals, substantial numbers of patients and their tissue samples can be screened and answers to such questions as the prevalence of MAP infection in populations at risk as a whole can be investigated economically. Antibody binding to synthetic peptide sequences is sequence dependent rather than conformation dependent, enabling the method to operate successfully on such samples.

The protocol for antigen retrieval and immunostaining of paraffin embedded tissue sections using the rabbit polyclonal antibodies was optimised as follows as follows: 0.2 µm tissue sections were de-paraffinised for 10 mins in 3 changes of xylene, rehydrated in descending grades of alcohol and placed in tap water for 5 mins. Antigen retrieval was achieved by immersing slides in distilled water containing 0.05% protease XIV *Streptomyces* Griseous Sigma P6911 P code 1000984453 at 37° C. for 5 mins. Slides were allowed to cool to room temperature and washed 3 times in 1×PBS each for 5 mins. Non-specific Fc receptor binding was blocked using Trustain@1/50 for 15 mins, and if required permeabilised in 0.1% Triton X-100 for 5 mins. Sections were washed briefly in 1×PBS and then incubated in primary antibody solution for 1 hour at room temperature on an orbital shaker. Sections were washed three times in 1×PBS each for 5 mins and incubated in secondary antibody conjugated with Dylite488/550 @1/1000 for 45 mins at room temperature (RT). Sections were washed three times in 1×PBS each for 5 mins, dehydrated, cleared in Xylene, mounted in aqueous mountant (Vectashield) and cover slipped.

Phase 3. Preparation of Murine Monoclonal Antibodies to Optimised P900 Peptide Sequences within the Selected A0, A1, A3 and A4 Sites and Phosphorylated Derivatives.

At this stage, an additional target site for monoclonal antibody production designated A0 was introduced comprising the sequence MVINDDAQRL (SEQ ID NO: residues 26-39 in the extracellular aminoterminal domain of P900. Few identical matches to this sequence were found in NCBI databases.

The production of murine monoclonal antibodies was first attempted in the following manner. Immunogen peptides in each case incorporating a solitary Cys thiol for linkage to KLH were prepared for A0 (MVINDDAQRL-C)(SEQ ID NO: 41), A3 (C-NLKRPRRYDR)(SEQ ID NO: 42) and A4 (C-VSIRTDPSSR)(SEQ ID NO: 43) and 5 mice were immunized in each group. Despite good immunological responses in some of the mice in each group, no monoclonals recognising their native targets in tissues were obtained. This was found to be due to the exclusive use of the target peptide for screening ELISAs and clonal selection being coated directly on to ELISA plate wells. This resulted in substantial artifact and the project was a comprehensive failure.

On the other hand the inventor found that it was essential for the target synthetic peptides used in screening ELISAs to be alpha-n Biotinylated and attached to wells coated with streptavidin. This increased the steric accessibility of the attached mobile peptides and permitted the adoption of the appropriate configuration of the peptide for antibody in the liquid phase. There was close correlation between antibody binding to target peptide in this form in ELISAs and to the native peptide in target tissues.

The essential Streptavidin coating and Biotinyl-peptide immobilisation in ELISA wells was adopted and used throughout the next project. During this project, mouse sera and culture supernatants were selected for binding to Reference peptide but not Negative peptides. Selected samples were subsequently tested by immunofluorescence on human and animal tissues and cells infected with MAP.

Immunogens were synthesised using the peptide sequences A0X MVINDDAQRLLSQR-C(SEQ ID NO: 44), A1 VTTLADGGEVTWAID-C(SEQ ID NO: 45), and XA4 YLSALVSIRTDPSSR-C(SEQ ID NO: 46) in each case the Cys thiol was used to link to KLH using standard methods. These constructs were used to immunise groups of 5 to 10 BalbC mice. Good serological responses to immunisation occurred in all groups and promising candidate clones were obtained for each group. Despite additions to immunisation protocols including in vitro immunisation and follow on immunisation using different immunogen adducts together with much additional work, no suitable final stable IgG clones could be obtained.

The materials used initially in the next project were as follows:

| | |
|---|---|
| Immunogen Peptide A0 ac-MVINDDAQRL-8branchedPolylysineOctamer (SEQ ID NO: 47) | |
| Reference peptide | Biotinyl-MVINDDAQRL-amide (SEQ ID NO: 48) |
| Negative peptide 1 | Biotiny-MVINDDLQR-amide (SEQ ID NO: 49) |
| Negative peptide 2 | Biotinyl-MVINNDAE-amide (SEQ ID NO: 50) |
| Immunogen peptide A1 ac-VTTLADGGEVT-8branchedPolylysineOctamer (SEQ ID NO: 51) | |
| Reference peptide | Biotinyl-VTTLADGGEVT-amide (SEQ ID NO: 52) |
| Negative peptide 1 | Biotinyl-VATMADGGEVT-amide (SEQ ID NO: 53) |
| Negative peptide 2 | Biotinyl-VTRLADGGEVT-amide (SEQ ID NO: 54) |
| Immunogen peptide A3 ac-NLKRPRRYDR-8branchedPolylysineOctamer (SEQ ID NO: 55) | |
| Reference peptide | Biotinyl-NLKRPRRYDR-amide (SEQ ID NO: 56) |
| Negative peptide 1 | Biotinyl-NLKRPRR-amide (SEQ ID NO: 57) |
| Negative peptide 2 | Biotinyl-NLRRPRRYHR-amide (SEQ ID NO: 58) |
| Negative peptide 3 | Biotinyl-NLHRPRRYHR-amide (SEQ ID NO: 59) |
| Negative peptide 4 | Biotinyl-NMRRPRRYNR-amide (SEQ ID NO: 60) |
| Negative peptide 5 | Biotinyl-NLRRPKRYNR-amide (SEQ ID NO: 61) |
| Negative peptide 6 | Biotinyl-NLQRPRRYNR-amide (SEQ ID NO: 62) |
| Immunogen peptide A4 ac-VSIRTDPSSR-8branchedPolylysineOctamer (SEQ ID NO: 63) | |
| Reference peptide | Biotinyl-VSIRTDPSSR-amide (SEQ ID NO: 64) |
| Negative peptide 1 | Biotinyl-VSIRTDP-amide (SEQ ID NO: 65) |
| Negative peptide 2 | Biotinyl-SIRSDPSSR-amide (SEQ ID NO: 66) |
| Negative peptide 3 | Biotinyl-YSIRSDPASR-amide (SEQ ID NO: 67) |
| Negative peptide 4 | Biotinyl-VSVRYDPSSR-amide (SEQ ID NO: 68) |
| Negative peptide 5 | Biotinyl-IAIRTDPASR-amide (SEQ ID NO: 69) |

Groups of 5 Swiss Webster mice were immunised with the immunogen peptide constructs in Freund's Complete Antigen on day 1 followed by 2 booster shots on day 14 and day 21 using Freund's Incomplete antigen. Boosting was continued but it was clear that none of the 4 groups were responding satisfactorily. Fresh peptide immunogens ac-MVINDDAQRL-C(SEQ ID NO: 70), ac-VTTLADG-GEVT-C(SEQ ID NO: 71), ac-NLKRPRRYDR-C(SEQ ID NO: 72), and ac-VSIRTDPSSR-C(SEQ ID NO: 73) were synthesised, coupled via the C- to KLH and immunisations continued.

Transient responses in the A0 and A1 groups were not sustained. Both flatlined and were terminated.

Serum from one mouse in each of the A3 and A4 groups achieved a sufficient titre to proceed to fusion and development of parental clones. A satisfactory subclone was not subsequently obtained for A3 and this project was terminated. A satisfactory subclone was achieved for A4 which recognised the reference peptide and none of the 5 negative peptides and was taken through final production and Protein A affinity purification.

At this stage three further modifications were introduced into the protocol:
1. The use of Balb/C mice.
2. Adoption of the technique of administering the immunogen at the base of the tail vein followed by direct fusion of pooled cells from inguinal lymph nodes.
3. Redesigned projects with the following new peptide immunogens.

| | |
|---|---|
| Immunogen peptide A0X C-MVINDDAQRLLSQR-amide (SEQ ID NO: 74) | |
| Reference peptide | Biotinyl-MVINDDAQRLLSQR-amide (SEQ ID NO: 75) |
| Negative peptide 1 | Biotinyl-MVINDDLQRIILFL-amide (SEQ ID NO: 76) |
| Negative peptide 2 | Biotinyl-MSINDDAQKLKDRL-amide (SEQ ID NO: 77) |
| Immunogen peptide A0XP C-MVINDDAQRLL[pS]QR-amide BSA conjugated (SEQ ID NO: 78) | |
| Reference peptide | Biotinyl-MVINDDAQRLL[pS]QR-amide (SEQ ID NO: 79) |
| Negative peptide 1 | Biotinyl-MVINDDAQRLLSQR-amide (SEQ ID NO: 80) |
| Immunogen peptide XA1 ac-d AAVTTLADGGEVTWAIDGKK-C BSA conjugate (SEQ ID NO: 81) | |
| Reference peptide | Biotinyl-KKGAAVTTLADGGEVTWAID-amide (SEQ ID NO: 82) |
| Negative peptide 1 | Biotinyl-KKGAAGTTLADGGEVTWAID-amide (SEQ ID NO: 83) |
| Negative peptide 2 | Biotinyl-KKGSTVATMADGGEVTWAID-amide (SEQ ID NO: 84) |
| Negative peptide 3 | Biotinyl-KKGQAVTRLADGGEVTWAVD-amide (SEQ ID NO: 85) |
| Negative peptide 4 | Biotinyl-KKGFEVTTLADGTEVATSPL-amide (SEQ ID NO: 86) |

The addition of the two Alanine residues to the amino terminus at this site was designed to increase immunogenicity and specificity. The addition of the charged –GKK residues at the carboxyterminus of the immunogen peptide was designed to overcome its increased hydrophobicity. In the event that the immunogen peptide formed micelles during the coupling reaction the presence of the charged GKK moiety adjacent to the Cysteine thiol would favour its accessibility to the BSA. The inclusion of mirror image KKG- at the aminoterminus of the reference peptide would favour the selection of antibody specific for the target sequence itself

| Immunogen peptide XA4P C-YLSALVSIRTDPS [pS]R-amide BSA conjugated (SEQ ID NO: 87) | |
|---|---|
| Reference peptide | Biotinyl-YLSALVSIRTDPS[pS]R-amide (SEQ ID NO: 88) |
| Negative 1 peptide | Biotinyl-YLSALVSIRTDPSSR-amide (SEQ ID NO: 89) |
| Negative peptide 2 | Biotinyl-YLSALYSIRSDPA[pS]R-amide (SEQ ID NO: 90) |
| Negative peptide 3 | Biotinyl-YLSALVSVRYDPS[pS]R-amide (SEQ ID NO: 91) |
| Negative peptide 4 | Biotinyl-YLSAQIAIRTDPA[pS]R-amide (SEQ ID NO: 92) |

All five A0X, A0XP, XA1, A4 and XA4P projects incorporating clonal selection for Reference peptide recognition by ELISA with limited or no binding to Negative Control peptides, followed by tissue and cell staining by selected clonal supernatants binding to tissues and cells, have been brought to successful conclusions. Affinity purified A0X, A0XP, XA1, A4 and XA4P monoclonals were obtained.

Example 2: Uses of the Diagnostic Technology for the Detection and Characterisation of MAP Infections in Samples from Humans and Animals and in Food Safety 1. Detection and Measurement of MAP Infecting Human Gut Tissues Endoscopic biopsies were studied from 45 people with Crohn's disease and some other disorders such as Irritable Bowel Syndrome (Scanu et al. *Mycobacterium avium* subspecies paratuberculosis infection in cases of Irritable Bowel Syndrome and comparison with Crohn's disease and Johne's disease: common neural and immune pathogenicities. J Clin Microbiol 2007: 45:3883-90). Samples were immediately fixed in formalin, followed by standard processing and embedding in paraffin Histopathology blocks. Preliminary work was carried out which identified 2 μm sections as optimal. Sections were treated with a standard antigen retrieval protocol. They were then stained with dilutions of monoclonal antibodies in the range 1 in 500 to 1 in 5000. Both direct fluorophore labelling of primary antibodies as well as the use of secondary antibodies labelled with fluorophore were employed. Tissues were stained with each of the primary antibodies A0X, A0XP, XA1, A4, XA4P used alone and viewed with using a Zeiss AxioSkop 2 microscope at magnifications of ×100 and ×200 to obtain a general impression of the distribution of MAP and then subsequently at ×400 and ×1000. MAP in humans is a Ziehl-Neelsen (Z-N) staining negative form and appears to be in the size range 0.3-1 μm. Higher magnification is required for satisfactory resolution.

A0X, XA1, A4 and XA4P all stained MAP in human gut, more specifically in endoscopic biopsies of the gut in all of the 45 people with Crohn's disease tested. However, staining of human gut tissues by A0XP was not seen in humans other than the occasional fluorescent signal from the lumen of a tissue blood vessel containing an A0XP positive cell in the blood. Unlike in animals, phosphorylation of A0X does not appear to occur widely in human gut. Phosphorylated A0XP however is seen in human blood in MAP infections. Staining of MAP by A0X, A0XP, XA1, A4 and XA4P is seen in human blood in MAP infection and in all people with Crohn's disease tested.

Antibodies were also used in combinations and viewed by confocal microscopy. Preferably antibodies were used in pairs. Preferred pairs were A0X with A0XP or XA1 from the amino terminus of the parent MAP molecule, and A4 with XA4P from the carboxyterminal end. Preferred pairs were also A0X with A4 and XA1 with A4 labelled with a red or green fluorophore respectively. This provided gold staining when the reagents colocalised specifically in the cytoplasm, not only of the same cells, but on the sub-micrometre MAP particles within the cytoplasm of infected cells. Such colocalisation provided strong confirmation of the specificity of MAP detection.

The use of antibody pairs comprising XA1 with A4 and A0X with A4 revealed a further aspect of the method. This is because whereas A0X and XA1 appeared to remain attached to the MAP organism itself or released to remain in the cell or displayed on the cell surface, A4 is frequently released from MAP to become displayed on the cell surface as well as released from the infected cell to traffic between cells. When A0X or XA1 are labelled with a red fluorophore and A4 labelled with a green one, the original gold colocalisation is progressively depleted to orange, and then to red as the green labelled A4 traffics to and enters other cells. Membrane bound structures filled with A4 green were seen, consistent with the presence of intercellular vesicles.

Biopsy samples from all the patients with Crohn's disease tested positive for MAP. This was observed in cells of the mucosal compartment, particularly the basal portion of the epithelial cells and the cytoplasm surrounding the basal portion of the mucus in goblet cells. Other MAP containing cells in the mucosal compartment were intra-epithelial macrophages and dendritic cells as well as intra-epithelial lymphocytes. MAP containing cells and free bacilli were also observed in the luminal mucus gel layer. In the lamina propria MAP infection was common in macrophages, polymorphs and B-lymphocytes. T-lymphocytes were rarely seen to be involved themselves, but frequently occurred adjacent to MAP filled macrophages. MAP positive cells were frequently seen in the lumen of small blood vessels. In duodenal biopsies MAP staining of Brunner's glands was limited only to the occasional macrophage filled with MAP while the glandular cells themselves were unaffected. However MAP containing cells were present in the interstitial connective tissue of Brunner's glands. A0XP in cells within tissues appeared to concentrate around the nucleus. These images of MAP in human tissues can be adapted to become quantitative and enable monitoring of the MAP infective load.

Surgical resection samples were also available from 4 patients with Crohn's disease. These samples permitted the examination not only the deeper layers of the gut through to the serosa, but also larger blood vessels, lymphatic vessels, extra intestinal fat wrapping and regional lymph nodes in the gut mesentery. As with the biopsy tissues the mucosa and sub-mucosa of each of these 4 patients were strongly positive for MAP. It was also found that the MAP infection extended right through the wall of the gut involving lymphatic vessels, the tissue between muscle layers and the serosa itself. In some sections lymphatic vessels full of stained MAP organisms were seen.

It has long been known that one of the pathological features of Crohn's disease is a vasculitis deemed to be autoimmune. The diagnostic antibodies showed that the thickened walls of such blood vessels were extensively infiltrated with MAP which also involved the surrounding perivascular connective tissues. Another characteristic pathological feature of Crohn's disease is the increase in fatty tissue around the gut. This is particularly well seen in the terminal ileum where it is termed 'fat wrapping'. The adipocytes of this fat are known to be a rich source of the inflammatory marker CRP (C-reactive protein). The diagnostic method showed that the thin cytoplasm of the adipocytes in this tissue were extensively infected with MAP. Abundant MAP was also seen in cells of the interstitial connective tissues within the fat. MAP was also seen to involve regional lymph nodes.

The gut tissues of all 5 people diagnosed with Irritable Bowel Syndrome (IBS) who were tested were also seen to be widely infected with MAP in a manner very similar to CD. Positive MAP staining of gut endoscopic biopsies was also seen in cases of Thyroditis and Psoriasis.

2. Animal Gut Tissues

Gut tissue samples were studied from 3 cows, 1 sheep, 1 goat, 1 red deer and 2 fallow deer all diagnosed with Johne's disease (JD). Autopsy samples were processed and stained with the primary antibodies, as described for humans. Tissues from all the animals were extensively infected with MAP which was generally present in the Ziehl-Neelsen positive phenotype. MAP in the guts of these animals diagnosed with Johne's disease stained with the A0X, A0XP, A4 and XA4P antibodies as well as with XA1. The microscopic appearance of MAP in animals was usually that of the classical Z-N positive mycobacterial phenotype but the monoclonal antibodies of the present work also demonstrated the pathogens in the paucimicrobial form.

The infective load of MAP in animals with Johne's disease was heavier than that found in humans in keeping with the well-recognised common pluribacillary form of JD. The MAP phenotype itself was consistent with ZN-positive cells. There was extensive involvement of mucosa and lamina propria and all layers of the gut. Cords of cells were seen which resulted from microvasculature full of MAP infected leucocytes. In addition, the thickened walls of vasculitic blood vessels and perivascular tissues were infiltrated with MAP infected cells as was seen in humans. MAP infection was also seen in neurovascular bundles affecting ganglion cells as well as nerve sheathes. This is consistent with the well described damage to the enteric nervous system of animals diagnosed with JD, much as in humans diagnosed with CD. A conspicuous difference between the gut tissues of these 5 ruminant species and humans is that A0XP is widely present in these animal gut tissues but appeared to be absent from human gut tissues.

3. Human Blood

Unlike in human gut tissues, A0XP, the phosphorylated form of A0X, is widely expressed in human blood. A0XP (MVINDDAQRLL[pS]QR (SEQ ID NO: 3)) is the Serine phosphorylated form of A0X peptide in the extracellular amino terminal region of the IS900 protein. XA4P (YLSAL-VSIRTDPS[pS]R (SEQ ID NO:6)) is the A4 peptide in the extracellular carboxyterminal region of the IS900 protein with the distal of its two adjacent Serine residues phosphorylated. In CD both A0XP and XA4P are expressed within and on the surface of MAP-containing cells in human blood.

This provides 2 pairs of sterically accessible mutually exclusive antibodies on the P900 polypeptide for use in flow cytometry with A0X/A0XP on the amino terminal extracellular domain and A4/XA4P on the carboxy terminal extracellular domain. Each pair exists in a dynamic equilibrium as substrate and product, the sum of which provides a robust signal for determining the percentage of peripheral blood leucocyte populations infected with intra-cellular MAP. A0X/A0XP either remain attached to MAP or can be released within the cell and on the infected host cell's surface. A4/XA4P provide a similar signal but A4 can exit MAP infected cells and traffic between cells so that the cell populations containing A4/XA4P comprise those containing MAP organisms with an additional smaller population in which the A4/XA4P has been acquired by inter-cellular trafficking.

Flow cytometry on routine EDTA clinical blood samples was performed on 42 people with Crohn's disease using direct fluorophore labelled A0X-FITC/A0XP-PC5.5 and A4-FITC/XA4P-PC5.5 in an exploratory study. All people tested positive for MAP, with the proportion of the total circulating white blood cell population positive for MAP ranging from 3.9% to 47.1%. Use of phenotypic markers of the principal blood cell lineages enables a breakdown according to host cell type. These proportions were generally greater with A4/XA4P than they were with A0X/A0XP. The ratios A0X/A0XP and A4/XA4P provided a measure of phosphorylation activity. A high ratio of XA4P/A4 tended to characterise people with Crohn's disease in a higher state of activity. In such people intact monocytes in blood completely coated with segregated masses of A4/XA4P could be seen.

A second flow cytometry was carried out in 24 consecutive patients with Crohn's disease to determine the proportion (%) of total circulating white blood cells containing MAP.

Blood samples were collected into standard EDTA Vacutainer tubes. 1000 of blood was then added to the required number of 12×75 mm round bottomed Falcon tubes. These were incubated for 5 minutes with 50 Human Seroblock (Bio-Rad). Anti-human CD45 APC conjugated antibody (Beckman Coulter) was added to all tubes to enable gating on the leucocyte populations. Half of the tubes (labelled 'surface stained') were then treated with the anti-MAP monoclonal antibodies for 15 minutes at room temperature in the dark. 0.5 mls OptiLyse C (Beckman Coulter) red blood cell lysis buffer was then added to all these tubes and incubated for 10 minutes at room temperature in the dark. The cells were then washed by adding 0.5 mls of PBS and centrifuged at 325G for 5 minutes and the supernatant discarded.

All tubes were then fixed with 1000 Fixation Medium A (Thermo Fisher Scientific) for 5 minutes then washed as above. The tubes that had not been stained with anti-MAP antibody (labelled 'Permeabilised') were incubated with Invitrogen Permeabilised Medium B (Thermo Fisher Scientific) to the pellet, anti-MAP monoclonal antibodies were added and incubated for 15 minutes at room temperature in the dark, followed by PBS washing as above. All tubes were then made up to 1ml with flow buffer (PBS (Ca and Mg free), 0.2% sodium azide and 2% Bovine Serum Albumin (BSA). The samples were then acquired on a CytoFLEX flow cytometer (Beckman Coulter) gated on SSC vs CD45 and subsequently the data was an analysed using CytExpert software (Beckman Coulter).

The results of the second study in 24 people with Crohn's disease are shown in the table below (Table 2). There were 8 women and 16 men between the ages of 18 and 49 years. The numbers in the table along the rows indicate the % of the total circulating white blood cell population in each person stained by the corresponding MAP antibody A0X alone, A0XP alone or both A0X+A0XP as well as A4 alone, XA4P alone or both A4+XA4P. Because the A0 antibodies remain attached to their target peptides for longer than the A4 antibodies, the SUM of the A0 data in an individual person were taken as the measure of the % of circulating WBCs containing MAP (highlighted centre column). This SUM varies with the progress, clinical course and responses to treatment of Crohn's disease providing a direct access to the contribution to pathogenicity made by this unique multicopy insertion element.

The Flow Cytometry data from A4, XA4P and A4+XA4P provides a second direct insight into a probable contribution to pathogenicity of MAP by recording a further aspect of the in vivo function of P900. This is the ability to observe the phosphorylation and trafficking of the attached and released carboxy terminus both with the phosphorylation of the downstream serine as in the present work and that of the upstream partner and the presence and effect of dual phosphorylation.

Table 1 summarises the Flow Cytometry data obtained from 24 patients with Crohn's disease based on the use of the monoclonal antibodies A0X and A0XP on the extracellular amino-terminus of P900 on the left of the table and A4 and XA4P on the extracellular carboxy-terminus of P900 on the right. The data for each patient in each row separate into binding to the surface of white blood cells (surf) and binding to whole permeabilised cells (perm). The total proportion of cells infected by MAP is given by the sum of the percentages % in separate permeabilised cell populations identified by A0X alone, A0XP alone and A0X+A0XP (highlighted). This is the preferred measurement because A0X peptides tend to remain bound to the host intracellular mycobacterial cells longer than A4 peptides. On the right of the table are the results using A4, XA4P and A4+XA4P stained cell populations. In this study the strongly predicted phosphorylation of the distal serine in XA4P is used but similar studies may target the phosphorylated proximal serine of the pair or in dual phosphorylation.

The potential of the data comes together when we look at detail. The % total MAP loading across the group of 24 patients ranges from 1.52% to 48.9% and appears at the present stage to vary with the activity of the disease. Peaks or troughs in the % of MAP positive cells may follow the onset of anti-MAP treatments. More data will come as larger numbers of people are tested and with different diseases particularly in the "autoimmune and auto inflammatory" group, and with access to the loading of individual cell types. More data will also be obtained from studying the clinical correlates of phosphorylation events and monitoring the effects of different treatments.

The data show that the proportion of cells with A0X/A0XP or both on their surfaces is about half. In the permeabilised cells, the total cell percentage with A0X/A0XP is in close agreement with that using A4/XA4P, whereas the sum of A4/XA4P on the cell surface is considerably less than with A0X/A0XP. This would be consistent with a greater loss of A4/XA4P from the cell surface which is in keeping with its recognised greater mobility. Studies of the effect of these phosphorylation events will require larger clinical studies.

The flow cytometry system is the first example to be developed for paratuberculosis infection in Crohn's disease. This can now be used to study MAP infection in other diseases including especially psoriasis, thyroiditis, Parkinson's disease, type 1 diabetes, arthritis, ankylosing spondylitis, irritable bowel syndrome, ulcerative colitis, inflammatory bowel disease, Alzheimer's disease, multiple sclerosis, sarcoidosis, idiopathic pulmonary fibrosis and/or chronic fatigue syndrome. With Crohn's disease as with these other diseases, particularly "autoimmune conditions", whether or not the presence of MAP is contributing to disease causation or progression will come from whether or not specific anti-MAP therapy leads to remission or healing of the disease. At present, the therapeutic T-cell vaccine against MAP is in early clinical trials.

TABLE 2

| MAP Monoclonal | | | A0X surf | A0XP surf | A0X + A0XP surf | A0X/A0XP SUM | A0X perm | A0XP perm | A0X + A0XP perm | A0X/A0XP SUM |
|---|---|---|---|---|---|---|---|---|---|---|
| Patient | M/F | Age | | | | | | | | |
| 1 | F | 32 | 5.67 | 0.7 | 1.49 | 7.86 | 25.02 | 2.93 | 1.11 | 29.06 |
| 2 | M | 48 | 2.37 | 4.94 | 4.85 | 12.16 | 7.52 | 12.42 | 10.87 | 30.81 |
| 3 | M | 29 | 7.59 | 0.05 | 1.30 | 8.94 | 7.66 | 5.71 | 8.33 | 21.70 |
| 4 | M | 28 | 1.50 | 0.19 | 3.07 | 4.76 | 4.90 | 1.12 | 0.29 | 6.31 |
| 5 | M | 37 | 0.90 | 0.77 | 1.37 | 3.04 | 11.02 | 10.33 | 0.19 | 21.54 |
| 6 | F | 40 | 16.15 | 0.76 | 0.37 | 17.28 | 20.62 | 0.30 | 0.76 | 21.68 |
| 7 | F | 25 | 10.43 | 0.38 | 0.73 | 11.54 | 23.13 | 0.41 | 1.09 | 24.63 |
| 8 | M | 39 | 1.32 | 6.62 | 2.08 | 10.02 | 2.32 | 8.12 | 5.01 | 15.45 |
| 9 | M | 20 | 37.93 | 0.17 | 0.02 | 38.12 | 45.82 | 0.44 | 1.83 | 48.09 |
| 10 | M | 33 | 14.81 | 1.45 | 0.31 | 16.57 | 23.05 | 2.88 | 13.98 | 39.91 |
| 11 | F | 48 | 3.95 | 1.8 | 1.49 | 7.24 | 4.92 | 1.97 | 1.71 | 8.60 |
| 12 | F | 26 | 1.06 | 0.74 | 1.89 | 3.69 | 2.39 | 1.65 | 2.00 | 6.04 |
| 13 | M | 27 | 1.39 | 1.65 | 2.00 | 5.04 | 3.42 | 2.61 | 2.02 | 8.05 |
| 14 | M | 29 | 2.28 | 2.3 | 1.86 | 6.44 | 2.31 | 5.01 | 2.36 | 9.68 |
| 15 | M | 29 | 1.95 | 12.86 | 4.99 | 19.80 | 3.40 | 15.85 | 5.71 | 24.96 |
| 16 | M | 25 | 0.02 | 1.32 | 0.03 | 1.37 | 0.11 | 1.41 | 0.00 | 1.52 |
| 17 | M | 37 | 0.24 | 0.33 | 0.05 | 0.62 | 11.40 | 11.39 | 5.81 | 28.60 |
| 18 | M | 18 | 1.26 | 1.96 | 6.63 | 9.85 | 1.78 | 3.41 | 5.39 | 10.58 |
| 19 | F | 48 | 1.79 | 2.79 | 2.96 | 7.54 | 2.62 | 5.96 | 5.15 | 13.73 |
| 20 | F | 18 | 0.92 | 5.15 | 0.64 | 6.71 | 1.22 | 5.67 | 1.20 | 8.09 |
| 21 | M | 20 | 11.78 | 0.36 | 8.85 | 20.99 | 15.41 | 0.30 | 9.28 | 24.99 |
| 22 | M | 49 | 0.35 | 1.27 | 0.80 | 2.42 | 1.58 | 1.97 | 2.76 | 6.31 |

TABLE 2-continued

| | | | | | | | | | | |
|---|---|---|---|---|---|---|---|---|---|---|
| 23 | M | 19 | 0.77 | 0.68 | 3.83 | 5.28 | 1.76 | 1.72 | 4.01 | 7.49 |
| 24 | F | 48 | 0.05 | 4.09 | 0.02 | 4.16 | 0.94 | 6.83 | 0.21 | 7.98 |
| SUM | | | | | | 231.44 | | | | 425.80 |
| average | | | | | | 9.64 | | | | 17.74 |

| MAP Monoclonal | | | A4 | XA4P | A4 + XA4P | A4/ XA4P | A4 | XA4P | A4 + XA4P | A4/ XA4P |
|---|---|---|---|---|---|---|---|---|---|---|
| Patient | M/F | Age | surf | surf | surf | SUM | perm | perm | perm | SUM |
| 1 | F | 32 | 3.14 | 6.63 | 5.98 | 15.75 | 3.91 | 19.76 | 6.88 | 30.55 |
| 2 | M | 48 | 5.47 | 1.19 | 0.13 | 6.79 | 7.54 | 1.27 | 2.29 | 11.10 |
| 3 | M | 29 | 3.09 | 3.70 | 1.44 | 8.23 | 9.05 | 4.23 | 2.82 | 16.10 |
| 4 | M | 28 | 3.54 | 1.00 | 0.34 | 4.88 | 5.85 | 0.23 | 1.25 | 7.33 |
| 5 | M | 37 | 0.31 | 1.42 | 0.90 | 2.63 | 6.85 | 19.24 | 2.94 | 29.03 |
| 6 | F | 40 | 1.20 | 0.14 | 0.21 | 1.55 | 1.25 | 2.77 | 1.88 | 5.90 |
| 7 | F | 25 | 2.59 | 0.14 | 0.50 | 3.23 | 2.89 | 12.09 | 31.62 | 46.60 |
| 8 | M | 39 | 8.35 | 8.73 | 6.09 | 23.17 | 11.92 | 10.83 | 12.83 | 35.58 |
| 9 | M | 20 | 0.41 | 0.00 | 0.12 | 2.50 | 19.89 | 5.76 | 3.01 | 28.66 |
| 10 | M | 33 | 21.26 | 0.03 | 1.23 | 22.52 | 7.90 | 0.84 | 41.03 | 49.77 |
| 11 | F | 48 | 2.20 | 0.02 | 0.28 | 2.50 | 2.35 | 4.17 | 1.72 | 8.24 |
| 12 | F | 26 | 0.45 | 0.15 | 0.10 | 0.70 | 2.77 | 0.96 | 0.81 | 4.54 |
| 13 | M | 27 | 2.17 | 0.96 | 0.81 | 3.94 | 3.04 | 1.46 | 1.35 | 5.85 |
| 14 | M | 29 | 0.30 | 6.31 | 2.50 | 9.11 | 2.33 | 11.74 | 7.91 | 21.98 |
| 15 | M | 29 | 0.00 | 0.56 | 2.45 | 3.01 | 0.00 | 6.98 | 8.26 | 15.24 |
| 16 | M | 25 | 0.68 | 0.64 | 0.46 | 1.78 | 1.38 | 1.37 | 0.47 | 3.22 |
| 17 | M | 37 | 0.05 | 2.24 | 0.14 | 2.43 | 2.27 | 4.31 | 1.09 | 7.67 |
| 18 | M | 18 | 0.36 | 9.11 | 1.53 | 11.00 | 0.42 | 13.6 | 1.76 | 15.78 |
| 19 | F | 48 | 1.04 | 3.40 | 3.60 | 8.04 | 2.43 | 4.88 | 8.14 | 15.45 |
| 20 | F | 18 | 5.12 | 0.53 | 2.61 | 8.26 | 5.62 | 0.85 | 5.61 | 12.08 |
| 21 | M | 20 | 0.85 | 2.70 | 0.36 | 3.91 | 19.92 | 4.1 | 6.84 | 30.86 |
| 22 | M | 49 | 8.80 | 0.31 | 7.08 | 16.19 | 9.06 | 0.58 | 9.12 | 18.76 |
| 23 | M | 19 | 0.38 | 0.21 | 0.21 | 0.80 | 2.06 | 0.76 | 0.41 | 3.23 |
| 24 | F | 48 | 0.00 | 6.76 | 4.62 | 11.38 | 0.49 | 7.81 | 4.91 | 13.21 |
| SUM | | | | | | 174.30 | | | | 436.73 |
| average | | | | | | 7.26 | | | | 18.20 |

3.2 Cytology

Cells isolated from peripheral blood were stained with a combination of two directly conjugated monoclonal antibodies: A0X (FITC/Green)+A0XP (Cy 5.5/Red) or A4 FITC/Green)+XA4P (Cy 5.5/Red). Confocal images were viewed using a Leica SP-2 confocal microscope, recorded and stored in JPEG format.

Results: peripheral blood cells showed considerable heterogeneity in their staining pattern with cells either negative, positive for a single antibody only, or positive for both antibodies. This latter observation is demonstrated by the clear co-localisation of the fluorescent reporter molecules. Although the phenotype of positive cells is yet to be established DIC (differential interference contrast) imaging and Flow cytometry data indicate that positive cells are non-lymphocytic in origin.

4. Animal Blood 4.1 Cats

A domestic cat (Cat 1) became unwell with weight loss, diarrhoea, distended abdomen and poor general condition. Ultrasound scan of the abdomen of the clinically affected animal showed thickening of the wall throughout the colon. Endoscopy and biopsy by the veterinarian showed clinically and histologically that the animal had Inflammatory Bowel Disease. Flow cytometry was performed on 2 EDTA blood samples over a period of 4 months. The proportion of total circulating white blood cells infected with MAP in the cat was 7.6% and 9.8%. Immunofluorescence microscopy on the endoscopic biopsy samples from Cat 1 confirmed the presence of MAP with a histological appearance similar to that seen in both animals with Johne's disease and humans with Crohn's disease.

During this period, a new kitten (Cat 2) was introduced to the same household. It was clinically well at the time of purchase from the breeder. A week following introduction to the household, the kitten developed bloody diarrhoea. Routine stool microbiology was negative. Flow cytometry was again performed on 2 EDTA blood samples over a period of 4 months. The proportion of circulating white cells infected with MAP was 16.4% and 14.3%. These data confirmed that both animals had a systemic MAP infection.

4.2 Dairy Cows

EDTA blood samples were obtained from 4 dairy cows. These animals were part of a closed dairy herd of more than 20 years standing with no known clinical cases of Johne's disease. Intermittent ELISA testing of individual milk samples from the herd had shown that one of the 4 sampled cows had had 2 positive ELISA readings and 2 other sampled cows had had 1 positive ELISA reading amongst multiple negative results. The fourth cow had had no raised ELISA readings on milk at all. Flow cytometry was performed on the 4 blood samples using A0X/A0XP and A4/XA4P pairs of monoclonal antibodies. The results showed that the proportions of the total circulating white blood cell populations in these animals infected with intracellular MAP, were 10.9%, 36.3%, 40.1%, and 45.2%. These results are a further indication of the ability of a significant systemic MAP infection to persist in a subclinical state. They also demonstrate that the present diagnostic technology has a much greater sensitivity than conventional diagnostic methods with the ability to reveal the true scale of the long term threat to animal and human health posed by these pathogens.

5. Human Breast Milk

A 3 month old male child presented with rectal bleeding and episodes of abdominal pain. He was investigated including upper and lower Gastrointestinal endoscopy with multiple biopsies, which led to the establishment of a diagnosis of Crohn's disease at 8 months. MAP tests, subsequently requested and carried out on his paraffin embedded histopathology blocks showed extensive infection with MAP of the stomach and duodenum and in all biopsies from the terminal ileum to the rectum. His mother, who did not have Crohn's disease, had never fed him anything except her own milk. However she had been diagnosed with auto-immune thyroiditis which is linked genetically to Crohn's disease. MAP testing requested by her on a 50 ml sample of expressed breast milk showed abundant MAP infected cells in the centrifugal pellet.

6. Human Skin Samples in Psoriasis 3-4 mm punch biopsy full thickness skin samples were obtained under local anaesthesia from 2 adults each diagnosed with Psoriasis. Samples were taken from the central region of a psoriatic skin lesion and an additional sample from the periphery of the lesion overlapping with normal skin. A normal skin sample between lesions was also obtained. Samples were formalin fixed, processed and embedded in routine histopathology blocks, following standard procedures. Sections of 2 µm were cut, immobilised on Vectabond microscope slides, treated for antigen retrieval, and stained with XA1/A4 monoclonal antibodies and examined by confocal microscopy.

Biopsies taken from within the psoriatic lesions were positive for MAP in both adults. Gold colocalisation of XA1 and A4 was seen in inflammatory cells in the thickened epidermal layer with staining persisting into the stratum corneum. Staining was also conspicuous in the germinal layer. Positive MAP staining extended throughout inflammatory cells in the rete and in inflammatory cells within the dermis. MAP positive cells were also seen around the hair follicles. A conspicuous associated feature was the presence of MAP within the pilo-sebaceous unit.

An abnormality of sebaceous glands might contribute to the dry, scaly nature of the superficial layers of psoriatic plaques. A further conspicuous feature in the dermis was MAP involvement of neurovascular bundles with colocalising XA1/A4 staining of these pathogens within thickened arterial walls and perivascular connective tissues. MAP staining of adjacent nerve bundles was also seen. Staining from biopsies taken at the periphery of psoriatic plaques showed that MAP staining stopped at the boundary between the plaque and normal skin. MAP was also absent from biopsies of normal looking skin between plaques. This would be consistent with a role for MAP in psoriatic plaque formation.

7. Measuring the Proportion of MAP Positive Cells in Synovial Joint Fluid in Arthritis An adult female human with Psoriasis presented with discomfort and an acute effusion in her right knee joint. There was no history of trauma. The joint was warm and distended but was not acutely tender. Other joints were unaffected. A 20 ml sample of straw coloured slightly opalescent fluid was aspirated and the cells separated by centrifugation. These were washed, stained with fluorophore labelled A0X/A0XP and examined by flow cytometry. The proportion of cells containing MAP in the joint fluid was 8.56%. This was similar to the % of MAP-positive peripheral white blood cells in her blood at the time.

8. Food Safety Testing

8.1 MAP Tests for Contamination of Retail Milk

MAP infection of farm animals has become a global problem. Human populations are widely exposed to MAP particularly in dairy products. New initiatives in the development of sufficiently sensitive diagnostic procedures in the veterinary and food sector are available using mass spectrometry, multiplex-bead based immunoassays and combined phage-PCR assay (Li et al. Early detection of *Mycobacterium avium* subsp. paratuberculosis infection in cattle with multiplex-bead based immunoassays. PLoS ONE 12(12): 2017 e0189783; Ricci M et al. Exploring MALDI-TOF MS approach for a rapid identification of *Mycobacterium avium* ssp. paratuberculosis field isolates Journal of Applied Microbiology 122, 568-577 2016; Botsaris G et al. Detection of viable *Mycobacterium avium* subspecies paratuberculosis in powdered infant formula by phage-PCR and confirmed by culture. International Journal of Food Microbiology Volume 216, 2016: 91-94).

There is an extensive literature on MAP diagnostic tests but in practise they are rarely applied commercially. This is generally because MAP is not widely recognised as a human pathogen and the available MAP test procedures at present require customised DNA extraction and PCR. New approaches are being taken in the veterinary sector using mass spectrometry and multiplex-bead based immunoassays.

The A0X, A0XP, XA1, A4 and XA4P anti-MAP antibodies can be used singly and together accessing available read-out systems, such as, for example, Flow Cytometry and Mass Spectrometry, to provide quantitative economic sensitive and automatable detection systems.

8.2 MAP Tests for Contamination of Meat

MAP contamination of the surface of meat can occur in abattoirs. Whereas destruction of these organisms would occur during normal cooking, this might not be the case for ground beef where they would be dispersed throughout the meat sample. Little is known at present of the distribution of MAP in bovine skeletal muscle because of the lack of a sensitive specific method for detecting MAP microscopically. The present diagnostic technology was applied to meat samples obtained from 10 cows, each of which was suspected of being MAP infected. Samples of skeletal muscle from each of the animals was tested initially by laboratory culture of MAP followed by PCR on the culture. Five of the cows had proved positive and 5 negative. In the present diagnostic method samples were fixed in formalin, processed and paraffin embedded following standard histopathology procedures. 3 µm sections were taken from each block and processed by antigen retrieval followed by staining with pairs of antibodies comprising A1/A4 and A0X/A4 and A0X/A0XP. Positive samples were ranked 1 (low) to 5 (high) according to the severity and distribution of MAP.

Nine of the 10 samples tested MAP positive, 2 at level 1, 3 at level 2, 2 at level 3 and 1 each at levels 4 and 5. MAP positive cells were seen to align along the sarcolemma of muscle fibres and within interfibrillary spaces. From level 3 upwards MAP extended right throughout the substance of the sample with organisms and their peptide products within muscle fibres as well as between them. Clusters of free MAP organisms invading muscle fibres were seen to disrupt their structure with some foci of apparent necrosis. The extent of MAP involvement throughout large areas of muscle was conspicuously greater than had previously been expected.

9. Testing Environmental Samples Such as Surface Waters, Rivers, Water Treatment Plants, Domestic Water Systems, Aerosols and Samples of Soil and Sediments.

The technical difficulties which have affected MAP testing of clinical samples also apply to those used in testing MAP in samples from river catchments, between release from an infected animal into the environment, to human exposure. The A0X, A0XP, XA1, A4, and XA4P antibodies and their corresponding MAP peptides in the present work may be used to capture and measure MAP and MAP peptides.

Example 3: Specificity of Antibodies for MAP

1. Staining of Cultured MAP and Related Mycobacteria in their Extracellular Phenotype.

Mycobacterial culture. Two strains of *Mycobacterium avium* subspecies paratuberculosis (MAP) K10 and M47508 were grown on Herold's egg yolk agar slants with Mycobactin J (BD BBL prepared media). Purity was monitored by using Herrold's egg yolk agar slants without Mycobactin J (BD BBL). Non-Mycobacterium strains were grown on Middlebrooks 7H10 agar plates (BD BBL). When growth was observed, individual colonies were suspended in 1 ml PBS and centrifuged at 13,000 rpm for 1 minute in a micro centrifuge, the supernatant removed and the pellet suspended in 1 ml PBS:

Mycobacterial staining: 200 µl of cultured cells were aliquoted onto Vectabond (Vector Laboratories, Peterborough UK) coated slides and when air dried and fixed with 10% formalin (BDH) for 30 mins. Slides were washed three times in 1×PBS (PH 7.4) and incubated at 37° overnight to ensure adhesion. Permeabilisation of the mycobacterial envelope was achieved by incubation in lysozyme (2 mg ml, prepared in water) followed by 5 min at room temperature with 0.1% triton X-100. Non-specific Fc receptor binding was blocked by incubating the slides with TrueStain FcX (Cambridge BioScience, Cambridge UK) @1/50 for 30 mins followed by a brief wash in 1×PBS. In order to establish antibody specificity a duplicate set of slides were stained in which the individual monoclonal antibodies had been incubated with their corresponding peptides for 1 hr at a concentration of 0.5 mg/ml prior to incubation. Slides were then incubated in primary antibody at the following dilutions: A0X (1/1500), A0XP (1/2500), A4 (1/1500), XA4P (1/2500) overnight at 4° C. on an orbital shaker. Sections were washed three times in 1×PBS each for 5 mins and incubated in secondary antibody conjugated with Dylite 550 (Thermo Fisher Scientific UK) @1/1500 for 45 mins at RT. Sections were washed three times in 1×PBS each for 5 mins before mounting in Aqueous mountant (Sigma F4680). Results: A0X, A0XP, A4 and XA4P monoclonal antibodies showed positive staining for both MAP cultures K10 and M47508 but were negative for all closely related strains tested (see Table 3). Staining of MAP cultures was absent when blocked with corresponding peptides but present when antibodies were incubated with non-corresponding peptides. These data indicate unique specificity of these four monoclonal antibodies for laboratory cultured MAP and not for the selected closely related species.

TABLE 3

| Mycobacterial strain | Antibody | Blocking Peptide A0X | Blocking Peptide A0XP | Blocking Peptide A4 | Blocking Peptide XA4P |
|---|---|---|---|---|---|
| K10 | A0X | − | + | + | + |
| K10 | A0XP | + | − | + | + |
| K10 | A4 | + | + | − | + |
| K10 | XA4P | + | + | + | − |
| M47508 | A0X | − | + | + | + |
| M47508 | A0XP | + | − | + | + |
| M47508 | A4 | + | + | − | + |
| M47508 | XA4P | + | + | + | − |
| *M avium* ssp *avium* | A0X | − | − | − | − |
| *M avium* ssp *avium* | A0XP | − | − | − | − |
| *M avium* ssp *avium* | A4 | − | − | − | − |
| *M avium* ssp *avium* | XA4P | − | − | − | − |
| *M avium* ssp *sylvat* | A0X | − | − | − | − |
| *M avium* ssp *sylvat* | A0XP | − | − | − | − |
| *M avium* ssp *sylvat* | A4 | − | − | − | − |
| *M avium* ssp *sylvat* | XA4P | − | − | − | − |
| *M avium* 2333 | A0X | − | − | − | − |
| *M avium* 2333 | A0XP | − | − | − | − |
| *M avium* 2333 | A4 | − | − | − | − |
| *M avium* 2333 | XA4P | − | − | − | − |
| *M avium chelonae* | A0X | − | − | − | − |
| *M avium chelonae* | A0XP | − | − | − | − |
| *M avium chelonae* | A4 | − | − | − | − |
| *M avium chelonae* | XA4P | − | − | − | − |
| *M porcinum* | A0X | − | − | − | − |
| *M porcinum* | A0XP | − | − | − | − |
| *M porcinum* | A4 | − | − | − | − |
| *M porcinum* | XA4P | − | − | − | − |
| *M Rhodesiae* | A0X | − | − | − | − |
| *M Rhodesiae* | A0XP | − | − | − | − |
| *M Rhodesiae* | A4 | − | − | − | − |
| *M Rhodesiae* | XA4P | − | − | − | − |
| *M thermoresistibile* | A0X | − | − | − | − |
| *M thermoresistibile* | A0XP | − | − | − | − |
| *M thermoresistibile* | A4 | − | − | − | − |
| *M thermoresistibile* | XA4P | − | − | − | − |

2. Staining of MAP and Related Mycobacteria in their Intracellular Phenotype in U937 Cell Culture.

Cell culture: U937 a human pro-monocytic cell line was grown in RPMI 1640 plus 10% foetal calf serum (FCS) and 100 U/ml penicillin and 100 µl/ml streptomycin at 37° C. in a humidified atmosphere with 5% $CO_2$.

Infection: When the U937 cells were in exponential growth phase they were counted, and viability assessed. $2×10\,5$ cells/ml at 95% viability were cultured in 2 mls RPMI 1640 plus 10% foetal calf serum (FCS) without antibiotics and challenged with *Mycobacterium paratuberculosis* K10 at an infection ratio of approximately 10:1. The cells were then incubated at 37° C. in a humidified atmosphere with 5% $CO^2$ for 5 hours, then resuspended in 2 mls of fresh growth media and cultured for a further 48 hours.

Staining: Four separate aliquots of cells containing $2×10^5$ cells/ml were taken and centrifuged at 1200 rpm for 5 mins. Cells were washed by re-suspension in 5 mls of PBS and centrifuged at 1200 for 5 mins. This was repeated three times. Monoclonal antibodies A0X, A0XP, A4 and XA4P were conjugated with either Fluorescein (Innova Biosciences kit 707-0015) or PE-Cy 5.5 (kit 761-0015) and then added to the cells so that the final concentrations of antibodies were 1/1500, 1/2500, 1/1500, 1/2500 respectively. Cells were left to incubate at room temperature for 1 hr, washed three times by the addition of ×3 volume of 1×PBS (PH 7.4) and centrifugation at 1500 rpm. 2000 of stained cells were aliquoted onto a Vectabond (Cole-Parmer, St. Neots, UK) microscope slide and viewed using a Leica SP2 confocal microscope.

Results: Immunofluorescence microscopy using the four directly conjugated monoclonal antibodies A0X, A0XP, A4 and XA4P identified positive Intracellular localisation of the MAP strain K10 within the pro-monocytic cell line U937. Localisation was confirmed using DIC (differential interference contrast) imaging.

3. ELISAs of A0X, A0XP, A4 and XA4P Monoclonal Anti-MAP Antibodies Binding to the Same Peptides and Related Peptides in Other Organisms.

Arrangements were made with the Suppliers of the 4 principal anti-MAP monoclonal antibodies to carry out ELISAs on the final protein A affinity purified monoclonal reagents. Of great importance was the need to use Streptavidin coated ELISA plates to immobilise the synthetic target peptides in the wells via Biotin linkage. Coating the wells with synthetic peptide only was unsuitable for the antibodies to synthetic peptide immunogens in the present work.

A0X clone 18C2/1C2 mouse IgG1
Immunogen: BSA-MVINDDAQRLLSQR-amide (SEQ ID NO: 93)

|  | IgG | | | IgM | | |
| --- | --- | --- | --- | --- | --- | --- |
|  | 1:10,000 | 1:50,000 | 1:100,000 | 1:10,000 | 1:50,000 | 1:100,000 |
| Bio-MVINDDAQRLLSQR-amide (SEQ ID NO: 75) | 1.254 | 0.598 | 0.302 | 0.068 | 0.075 | 0.073 |
| Bio-MSINDDAQKLKDRL-amide (SEQ ID NO: 76) | 0.064 | 0.057 | 0.057 | 0.063 | 0.066 | 0.077 |
| Bio-MVINDDAQRLL[pS]QR-amide (SEQ ID NO: 77) | 0.061 | 0.056 | 0.057 | 0.063 | 0.065 | 0.069 |

A0XP clone 3D2/2C5 mouse IgG1
Immunogen: BSA-MVINDDAQRLL(pS)QR (SEQ ID NO: 94)

|  | IgG 1:1000 | IgM 1:1000 |
| --- | --- | --- |
| Bio-MVINDDAQRLL[pS]QR-amide (SEQ ID NO: 79) | 0.741 | 0.173 |
| Bio-MVINDDAQRLLSQR-amide (SEQ ID NO: 80) | 0.185 | 0.186 |

A4 clone 3F7A7/A12 mouse IgG2a
Immunogen: BSA-VSIRTDPSSR-amide (SEQ ID NO: 95)

|  | IgG | | | IgM | | |
| --- | --- | --- | --- | --- | --- | --- |
|  | 1:2000 | 1:5000 | 1:10,000 | 1:2000 | 1:5000 | 1:10,000 |
| Bio-VSIRTDPSSR-amide (SEQ ID NO: 64) | 0.577 | 0.386 | 0.194 | 0.068 | 0.064 | 0.074 |
| Bio-SIRSDPSSR-amide (SEQ ID NO: 66) | 0.082 | 0.068 | 0.064 | 0.069 | 0.064 | 0.081 |
| Bio-YSIRSDPASR-amide (SEQ ID NO: 67) | 0.088 | 0.07 | 0.062 | 0.068 | 0.067 | 0.072 |
| Bio-VSVRYDPSSR-amide (SEQ ID NO: 68) | 0.082 | 0.076 | 0.07 | 0.069 | 0.085 | 0.078 |
| Bio-IAIRTDPASR-amide (SEQ ID NO: 69) | 0.11 | 0.079 | 0.073 | 0.081 | 0.076 | 0.094 |

XA4P clone 2D4/1B5 mouse IgG2a
Immunogen: BSA-YLSALVSIRTDPS(pS)R-amide (SEQ ID NO: 96)

|  | IgG 1:2000 | IgM 1:2000 |
| --- | --- | --- |
| Bio-YLSALVSIRTDPS[pS]R-amide (SEQ ID NO: 88) | 1.329 | 0.146 |
| Bio-YLSALVSIRTDPSSR-amide (SEQ ID NO: 89) | 0.066 | 0.062 |
| Bio-YLSALYSIRSDPA[pS]R-amide (SEQ ID NO: 90) | 0.286 | 0.072 |
| Bio-YLSALVSVRYDPS[PS]R (SEQ ID NO: 91) | 1.374 | 0.134 |
| Bio-YLSAQIAIRTDPA[pS]R-amide (SEQ ID NO: 92) | 0.380 | 0.073 |

4. Differential Blockade of Antibody Staining of Tissues by the Identical Synthetic Target Peptide and not by Unrelated Peptides.

2 μm paraffin tissue sections were taken from the caecum and ascending colon of a Crohn's patient and individually stained with the four monoclonal antibodies A0X, A0XP, A4 and XA4P. In order to establish antibody specificity and exclude non-specific staining a parallel set of tissue sections were stained with the four monoclonal antibodies pre-incubated with 0.5 μg of synthetic peptide corresponding to the individual antigenic sequences.

Results: A0X staining identified clusters of MAP positive cells within the lamina propria and occasional cells within blood vessels. Signal was blocked to near completion by pre-incubation with A0X peptide. No apparent staining in of the human gut tissue in either blocked or un-blocked sections was observed when stained with A0XP. Staining with A4 showed occasional positive cells within the lamina propria which was partially blocked with prior incubation with A4 peptide. XA4P staining identified both intra and perivascular staining of MAP positive cells in addition to foci of positive cells within the lamina propria. Blockade with pre-incubation of XA4P peptide partially blocked this staining.

The invention claimed is:

1. A method of detecting *Mycobacterium avium* subspecies paratuberculosis (MAP) in a sample, wherein the method comprises obtaining the sample and detecting in the sample the presence of the polypeptide encoded by the positive strand of MAP IS900 (MAP P900), or a fragment thereof, by detecting an extracellular region of MAP P900, wherein the extracellular region of MAP P900 is selected from the group consisting of: MVINDDAQRLLSQR (SEQ ID NO: 2), MVINDDAQRLL[pS]QR (SEQ ID NO: 3), YLSALVSIRTDPSSR (SEQ ID NO: 4), VSIRTDPSSR (SEQ ID NO: 5), YLSALVSIRTDPS[pS]R (SEQ ID NO: 6), YLSALVSIRTDP[pS]SR (SEQ ID NO: 7), VSIRTDP[pS][pS]R (SEQ ID NO: 8), VSIRTDP[pS]SR (SEQ ID NO: 9), AAVTTLADGGEVTWAID (SEQ ID NO: 10), NLKRPRRYDRRLLRA (SEQ ID NO: 11), VTTLADGGEVTWAID (SEQ ID NO: 12), YLSALVSIRTDP[pS][pS]R (SEQ ID NO: 13) and VSIRTDPS[pS]R (SEQ ID NO: 98).

2. The method according to claim 1, wherein the detection of the extracellular region of MAP P900 comprises detecting two or more of the extracellular regions of MAP P900.

3. The method according to claim 2, wherein the detection of the two or more extracellular regions of MAP P900 comprises detecting:
- the extracellular region of MAP P900 defined by amino acids 26 to 71 of SEQ ID NO: 1 and the extracellular region of MAP P900 defined by amino acids 329 to 385 of SEQ ID NO: 1;
- the extracellular region of MAP P900 defined by amino acids 26 to 39 of SEQ ID NO: 1 and region of MAP P900 defined by amino acids 52 to 68 of SEQ ID NO: 1;
- the extracellular region of MAP P900 defined by amino acids 52 to 68 of SEQ ID NO: 1 and the extracellular region of MAP P900 defined by amino acids 345 to 359 or 350 to 359 of SEQ ID NO: 1; or
- the extracellular region of MAP P900 defined by amino acids 26 to 71 of SEQ ID NO: 1, wherein serine 37 is optionally phosphorylated and the extracellular region of MAP P900 defined by amino acids 345 to 359 or 350 to 359 of SEQ ID NO: 1, wherein serine 357 and/or serine 358 is optionally phosphorylated.

4. The method according to claim 3, wherein the method comprises determining whether the region of MAP P900 between amino acids 26 to 71 and/or 273 to 406 of SEQ ID NO: 1, or a fragment of either thereof, has been cleaved from membrane-bound MAP P900.

5. The method according to claim 4, wherein the method comprises determining whether the cleaved region of MAP P900, or fragment thereof, has spread from microbial cells and/or host cells containing membrane bound MAP P900.

6. The method according to claim 2, wherein the detection of the two or more extracellular regions of MAP P900 comprises the detection of at least one non-phosphorylated MAP P900 sequence and at least one phosphorylated MAP P900 sequence.

7. The method according to claim 6, wherein the non-phosphorylated MAP P900 sequence is MVINDDAQRLLSQR (SEQ ID NO: 2) and the phosphorylated MAP P900 sequence is MVINDDAQRLL[pS]QR (SEQ ID NO: 3); or the non-phosphorylated MAP P900 sequence is YLSALVSIRTDPSSR (SEQ ID NO: 4) or VSIRTDPSSR (SEQ ID NO: 5), and the phosphorylated MAP P900 sequence is YLSALVSIRTDPS[pS]R (SEQ ID NO: 6), YLSALVSIRTDP[pS]SR (SEQ ID NO: 7), YLSALVSIRTDP[pS][pS]R (SEQ ID NO: 13), VSIRTDPS[pS]R (SEQ ID NO: 98), VSIRTDP[pS]SR (SEQ ID NO: 9) or VSIRTDP[pS][pS]R (SEQ ID NO: 8).

8. The method according to claim 1, wherein the sample is obtained from a subject, wherein the subject is a human or an animal.

9. The method according to claim 8, wherein the sample is a sample of a body fluid or a tissue sample.

10. The method according to claim 9, wherein the body fluid is blood, semen, amniotic fluid, cerebrospinal fluid, synovial fluid or breast milk, or the tissue is skin, gastrointestinal tract, thyroid, lymph node, brain or genitourinary tract.

11. The method according to claim 8, wherein the sample is obtained from a subject having Crohn's disease, psoriasis, thyroiditis, Parkinson's disease, type 1 diabetes, arthritis, ankylosing spondylitis, irritable bowel syndrome, ulcerative colitis, inflammatory bowel disease, Alzheimer's disease, multiple sclerosis, sarcoidosis, idiopathic pulmonary fibrosis and/or chronic fatigue syndrome.

12. The method according to claim 1, wherein the sample is a food product.

13. The method according to claim 12, wherein the food product is milk or other dairy product or a meat product.

14. The method according to claim 1, wherein the sample is an environmental sample.

15. The method according to claim 14, wherein the environmental sample is a sample of surface water, river water, water-treatment plant water, domestic water, or an aerosol, soil or sediment.

16. A method of food safety testing, wherein the method comprises obtaining a food sample and detecting MAP in the food sample, wherein the detection of MAP comprises detecting the presence of MAP P900, or a fragment thereof, by detecting an extracellular region of MAP P900 in the food sample, wherein the extracellular region of MAP P900 is selected from the group consisting of: MVINDDAQRLLSQR (SEQ ID NO: 2), MVINDDAQRLL[pS]QR (SEQ ID NO: 3), YLSALVSIRTDPSSR (SEQ ID NO: 4), VSIRTDPSSR (SEQ ID NO: 5), YLSALVSIRTDPS[pS]R (SEQ ID NO: 6), YLSALVSIRTDP[pS]SR (SEQ ID NO: 7), VSIRTDP[pS][pS]R (SEQ ID NO: 8), VSIRTDP[pS]SR (SEQ ID NO: 9), AAVTTLADGGEVTWAID (SEQ ID NO: 10), NLKRPRRYDRRLLRA (SEQ ID NO: 11), VTTLADGGEVTWAID (SEQ ID NO: 12), YLSALVSIRTDP[pS][pS]R (SEQ ID NO: 13) and VSIRTDPS[pS]R (SEQ ID NO: 98).

17. A method of diagnosing and treating MAP infection in a human or animal subject, wherein the method comprises:
(a) detecting MAP, wherein the detection of MAP comprises detecting the presence of MAP P900, or a fragment thereof, in a sample from the subject, by detecting an extracellular region of MAP P900 in the sample, wherein the extracellular region of MAP P900 is selected from the group consisting of: MVINDDAQRLLSQR (SEQ ID NO: 2), MVINDDAQRLL[pS]QR (SEQ ID NO: 3), YLSALVSIRTDPSSR (SEQ ID NO: 4), VSIRTDPSSR (SEQ ID NO: 5), YLSALVSIRTDPS[pS]R (SEQ ID NO: 6), YLSALVSIRTDP[pS]SR (SEQ ID NO: 7), VSIRTDP[pS][pS]R (SEQ ID NO: 8), VSIRTDP[pS]SR (SEQ ID NO: 9), AAVTTLADGGEVTWAID (SEQ ID NO: 10), NLKRPRRYDRRLLRA (SEQ ID NO: 11), VTTLADGGEVTWAID (SEQ ID NO: 12), YLSALVSIRTDP[pS][pS]R (SEQ ID NO: 13) and VSIRTDPS[pS]R (SEQ ID NO: 98); and
(b) treating the human or animal subject in whom MAP is detected, optionally wherein the human or animal subject is treated with an antimicrobial agent, a therapeutic MAP vaccine or passive immunotherapy.

* * * * *